(12) United States Patent
Ueda et al.

(10) Patent No.: US 11,464,739 B2
(45) Date of Patent: Oct. 11, 2022

(54) FUNCTIONAL NANOSTRUCTURE

(71) Applicant: RIKEN, Saitama (JP)

(72) Inventors: Motoki Ueda, Saitama (JP); Yoshihiro Ito, Saitama (JP)

(73) Assignee: RIKEN, Saitama (JP)

( * ) Notice: Subject to any disclaimer, the term of this patent is extended or adjusted under 35 U.S.C. 154(b) by 0 days.

(21) Appl. No.: 16/734,946

(22) Filed: Jan. 6, 2020

(65) Prior Publication Data

US 2020/0214981 A1 Jul. 9, 2020

(30) Foreign Application Priority Data

Jan. 9, 2019 (JP) .............................. JP2019-001717

(51) Int. Cl.
*A61K 9/127* (2006.01)

(52) U.S. Cl.
CPC .......... *A61K 9/1272* (2013.01); *A61K 9/1277* (2013.01)

(58) Field of Classification Search
CPC ..... A61K 9/1272; A61K 9/1277; A61K 9/127
See application file for complete search history.

(56) References Cited

U.S. PATENT DOCUMENTS

| | | | |
|---|---|---|---|
| 5,789,542 A * | 8/1998 | McLaughlin | C12N 1/06 435/259 |
| 2006/0165766 A1 * | 7/2006 | Barenholz | A61P 43/00 424/450 |
| 2018/0326055 A1 * | 11/2018 | Ueda | A61K 39/3955 |
| 2020/0214981 A1 * | 7/2020 | Ueda | A61K 9/1277 |

OTHER PUBLICATIONS

Zahraa S. Al-Ahmady, Wafa T. Al-Jamal, Jeroen V. Bossche, Tam T. Bui, Alex F. Drake, A. James Mason, and Kostas Kostarelos. "Lipid-Peptide Vesicle Nanoscale Hybrids for Triggered Drug Release by Mild Hyperthermia in Vitro and in Vivo." ACS Nano, vol. 6, No. 10, 2012, pp. 9335-9346. (Year: 2012).*
Motoki Ueda, Stefan Müller, Siyoong Seo, Md. Mofizur Rahman, and Yoshihiro Ito. "Chapter 2 Integrated Nanostructures Based on Self-Assembled Amphiphilic Polypeptides." Advances in Bioinspired and Biomedical Materials vol. 1, 2017, pp. 19-30. (Year: 2017).*
J. N. Israelachvili, S. Marcelja, and R. G. Horn. "Physical principles of membrane organization." Quarterly Reviews of Biophysics 13, 2 (1980), pp. 121-200. (Year: 1980).*

(Continued)

*Primary Examiner* — Isaac Shomer
(74) *Attorney, Agent, or Firm* — Casimir Jones, S.C.; Tanya A. Arenson

(57) ABSTRACT

An object is to achieve a nanostructure that has structural stability and temperature responsivity. Provided is a nanostructure which is a hollow body constituted by a wall, the wall including a first region and a second region, the first region being formed from an assembly of a plurality of first amphiphilic molecules containing a hydrophilic block and a hydrophobic block, the second region being formed from an assembly of a plurality of second amphiphilic molecules which are different from the first amphiphilic molecules, the first region being arranged to be in its solid phase at a phase transition temperature at which the second region of the wall transitions from its solid phase to its liquid phase.

6 Claims, 10 Drawing Sheets

(56) References Cited

OTHER PUBLICATIONS

Md. Mofizur Rahman, Motoki Ueda, Takuji Hirose, and Yoshihiro Ito. "Spontaneous Formation of Gating Lipid Domain in Uniform-Size Peptide Vesicles for Controlled Release." Journal of the American Chemical Society, vol. 140, 2018, pp. 17956-17961, published Dec. 10, 2018. (Year: 2018).*
Akira Makino. "Morphology control of molecular assemblies prepared from bio-based amphiphilic polymers with a helical hydrophobic unit and application as nanocarriers for contrast agents and/or drug delivery." Polymer Journal, vol. 46 (2014), pp. 783-791. (Year: 2014).*
Tatsuya Kanzaki, Yoshiki Horikawa, Akira Makino, Junji Sugiyama, Shunsaku Kimura. "Nanotube and Three-Way Nanotube Formation with Nonionic Amphiphilic Block Peptides." Macromolecular Biosciences, vol. 8, 2008, pp. 1026-1033. (Year: 2008).*
Motoki Ueda, Akira Makino, Tomoya Imai, Junji Sugiyama and Shunsaku Kimura. "Versatile peptide rafts for conjugate morphologies by self-assembling amphiphilic helical peptides." Polymer Journal (2013) 45, 509-515. (Year: 2013).*
ScienceDaily. "'Islands' of cell membrane components—Proteoliposome fusion and domain formation in an artificial lipid bilayer membrane." https://www.sciencedaily.com/releases/2018/02/180201104609.htm accessed Nov. 1, 2021, originally published on Feb. 2, 2018, 3 printed pages. (Year: 2018).*
Matthew J. McKay, Fahmida Afrose, Roger E. Koeppe II, Denise V. Greathouse. "Helix formation and stability in membranes." BBA—Biomembranes, vol. 1860 (2018), pp. 2108-2117, available online Feb. 13, 2018. (Year: 2018).*
Ryugo Tero, Kohei Fukumoto, Toshinori Motegi, Miyu Yoshida, Michio Niwano, & Ayumi Hirano-Iwata. "Formation of Cell Membrane Component Domains in Artificial Lipid Bilayer." Scientific Reports, 7:17905, 2017, pp. 1-10. (Year: 2017).*
Shaw, A. W.; McLean, M. A.; Sligar, S. G. Phospholipid phase transitions in homogeneous nanometer scale bilayer discs. FEBS Lett. 2004, 556 (1-3), 260-264.
Denisov, I. G.; McLean, M. A.; Shaw, A. W.; Grinkova, Y. V.; Sligar, S. G. Thermotropic phase transition in soluble nanoscale lipid bilayers. J. Phys. Chem. B 2005, 109 (32), 15580-15588.
Viard, M.; Gallay, J.; Vincent, M.; Meyer, O.; Robert, B.; Patemostre, M. Laurdan solvatochromism: Solvent dielectric relaxation and intramolecular excited-state reaction. Biophys. J. 1997, 73 (4), 2221-2234.

Bakht, O.; Pathak, P.; London, E. Effect of the structure of lipids favoring disordered domain formation on the stability of cholesterol-containing ordered domains (lipid rafts): Identification of multiple raft-stabilization mechanisms. Biophys. J. 2007, 93 (12), 4307-4318.
Parasassi, T.; De Stasio, G.; Ravagnan, G.; Rusch, R. M.; Gratton, E. Quantitation of Lipid Phases in Phospholipid-Vesicles by the Generalized Polarization of Laurdan Fluorescence. Biophys. J. 1991, 60 (1), 179-189.
Parasassi, T.; Gratton, E. Membrane lipid domains and dynamics as detected by Laurdan fluorescence. J. Fluoresc. 1995, 5 (1), 59-69.
Parasassi, T.; Krasnowska, E. K.; Bagatolli, L.; Gratton, E. LAURDAN and PRODAN as polarity-sensitive fluorescent membrane probes. J Fluoresc. 1998, 8 (4), 365-373.
Cohen, C.; Parry, D. A. D. Alpha-Helical Coiled Coils and Bundles—How to Design an Alpha-Helical Protein. Proteins: Struct., Funct., Genet. 1990, 7 (1), 1-15.
Kornilova, A. Y.; Wishart, J. F.; Xiao, W. Z.; Lasey, R. C.; Fedorova, A.; Shin, Y. K.; Ogawa, M. Y. Design and characterization of a synthetic electron-transfer protein. J. Am. Chem. Soc. 2000, 122 (33), 7999-8006.
Lewis, B. A.; Engelman, D. M. Lipid Bilayer Thickness Varies Linearly with Acyl Chain-Length in Fluid Phosphatidylcholine Vesicles. J. Mol. Biol. 1983, 166 (2), 211-217.
Nakano, M.; Fukuda, M.; Kudo, T.; Miyazaki, M.; Wada, Y.; Matsuzaki, N.; Endo, H.; Handa, T. Static and Dynamic Properties of Phospholipid Bilayer Nanodiscs. J. Am. Chem. Soc. 2009, 131 (23), 8308-8312.
Kaindl, T.; Adlkofer, K.; Morita, T.; Umemura, J.; Konovalov, O.; Kimura, S.; Tanaka, M. Modulation of Band Bending of Gallium Arsenide with Oriented Helical Peptide Monolayers. J. Phys. Chem. C 2010, 114 (51), 22677-22683.
T. Kanzaki, Y. Horikawa, A. Makino, J. Sugiyama and S. Kimura, Nanotube and Three-Way Nanotube Formation with Nonionic Amphiphilic Block Peptides, Macromol. Biosci. 2008, 8(11), 1026-1033.
M. Ueda, A. Makino, T. Imai, J. Sugiyama and S. Kimura, Versatile peptide rafts for conjugate morphologies by self-assembling amphiphilic helical peptides, Polym. J. 2013, 45, 509-515.
M Ueda et al., Advances in Biosinpired and Biomedical Materials, American Chemical Society Symposium Series 1252, vol. 1, 19-30 (2017).

* cited by examiner

FUNCTIONAL NANOSTRUCTURE

TECHNICAL FIELD

This application claims priority on Japanese Patent Application, *Tokugan*, No. 2019-001717 (the contents of the specification thereof are hereby incorporated by reference).

The present invention relates to a nanostructure and a method of producing a nanostructure.

BACKGROUND ART

As nanotechnology has become increasingly important in recent years, various new functional materials, which make use of the properties specific to nano-sized substances, have been developed. Such nano-sized functional materials have been promising in applications to various fields such as energy, electronics, and pharmaceuticals. For example, in the field of pharmaceuticals, liposome, which is a nanoparticle composed of a phospholipid, or the like is used as a carrier in drug delivery system (DDS).

Furthermore, in regard to a nanostructure formed from peptides, Non-patent Literature 1 states that peptide nanostructures of various shapes were prepared from amphiphilic peptide chains having a hydrophilic block and a hydrophobic helical block.

CITATION LIST

Non-Patent Literature

[Non-Patent Literature 1]
M Ueda et al., Advances in Bioinspired and Biomedical Materials, volume 1, 19-30 (2017)

SUMMARY OF INVENTION

Technical Problem

There is a demand for development of a carrier for more efficient delivery of a drug. Under such circumstances, it is an object of an aspect of the present invention to obtain a nanostructure that has structural stability and temperature responsivity.

Solution to Problem

In order to attain the above object, a nanostructure in accordance with an aspect of the present invention is a hollow body constituted by a wall, the wall including a first region and a second region, the first region being formed from an assembly of a plurality of first amphiphilic molecules containing a hydrophilic block and a hydrophobic block, the second region being formed from an assembly of a plurality of second amphiphilic molecules which are different from the first amphiphilic molecules, the first region being arranged to be in its solid phase at a phase transition temperature at which the second region of the wall transitions from its solid phase to its liquid phase.

In order to attain the above object, a nanostructure in accordance with another aspect of the present invention is a hollow body constituted by a wall, the wall including a first region and a second region, the first region being formed from an assembly of a plurality of first amphiphilic molecules containing a hydrophilic block and a hydrophobic block, the second region being formed from an assembly of a plurality of second amphiphilic molecules which are different from the first amphiphilic molecules, the first amphiphilic molecules being amphiphilic peptide chains containing a hydrophilic peptide block and a hydrophobic peptide block, the second amphiphilic molecules being lipid molecules.

Advantageous Effects of Invention

According to an aspect of the present invention, it is possible to provide a nanostructure that has structural stability and temperature responsivity.

DESCRIPTION OF EMBODIMENTS (Overview)

Figure 1:
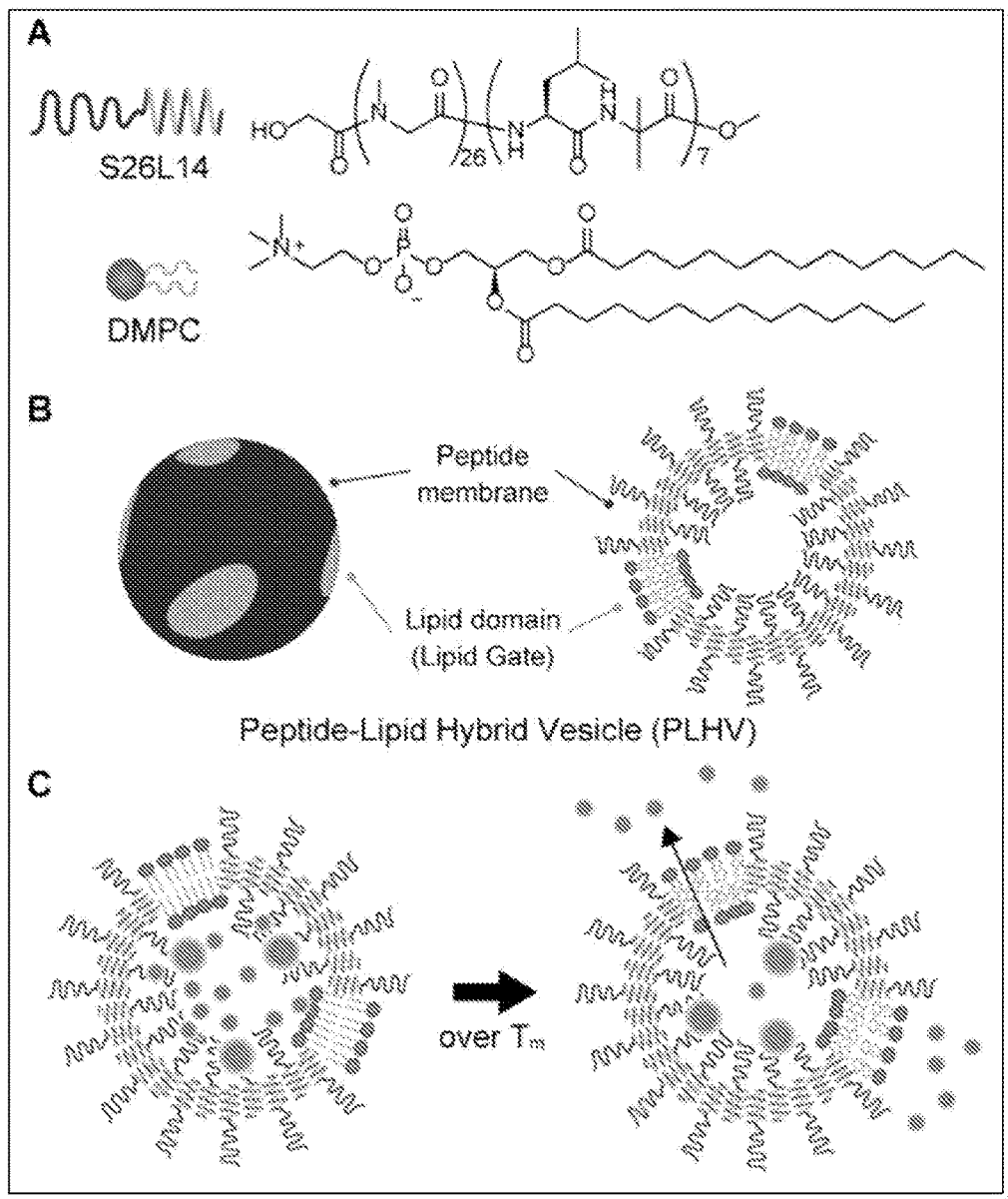
FIG. 1 schematically illustrates an example of a nanostructure.

A nanostructure in accordance with an aspect of the present invention is a hollow body constituted by a wall, the wall including a first region and a second region, the first region being formed from an assembly of a plurality of first amphiphilic molecules containing a hydrophilic block and a hydrophobic block, the second region being formed from an assembly of a plurality of second amphiphilic molecules which are different from the first amphiphilic molecules, the first region being arranged to be in its solid phase at a phase transition temperature at which the second region of the wall transitions from its solid phase to its liquid phase. The nanostructure in accordance with an aspect of the present invention has functions such as structural stability and temperature responsivity.

A nanostructure in accordance with another aspect of the present invention is a hollow body constituted by a wall, the wall including a first region and a second region, the first region being formed from an assembly of a plurality of first amphiphilic molecules containing a hydrophilic block and a hydrophobic block, the second region being formed from an assembly of a plurality of second amphiphilic molecules which are different from the first amphiphilic molecules, the first amphiphilic molecules being amphiphilic peptide chains containing a hydrophilic peptide block and a hydrophobic peptide block, the second amphiphilic molecules being lipid molecules.

(First Amphiphilic Molecule)

Examples of a first amphiphilic molecule include amphiphilic peptide chains. Note that a hydrophilic block included in a first amphiphilic molecule may be hereinafter referred to as "first hydrophilic block", and a hydrophobic block included in the first amphiphilic molecule may be hereinafter referred to as "first hydrophobic block".

The term "first hydrophilic block" refers to a region that shows hydrophilicity. There is no particular limitation on the degree of the physical property "hydrophilic" of the first hydrophilic block. The first hydrophilic block needs only be hydrophilic to the extent that the first hydrophilic block is more hydrophilic than other regions of a first amphiphilic molecule and that the first amphiphilic molecule, constituted by the first hydrophilic block and the other regions, as a whole can be amphiphilic. Alternatively, the first hydrophilic block needs only be hydrophilic to the extent that the first amphiphilic molecules are capable of becoming self-organized and forming a self-assembly in a medium.

The term "first hydrophobic block" refers to a region that shows hydrophobicity. There is no particular limitation on the degree of the physical property "hydrophobic" of the first hydrophobic block. The first hydrophobic block needs only be hydrophobic to the extent that the first hydrophobic block is more hydrophobic than other regions of a first amphiphilic molecule and that the first amphiphilic molecule, constituted by the first hydrophobic block and the other regions, as a whole can be amphiphilic. Alternatively, the first hydrophobic block needs only be hydrophobic to the extent that the first amphiphilic molecules are capable of becoming self-organized and forming a self-assembly in a medium.

In one example, the "first hydrophilic block" and the "first hydrophobic block" are adjacent to each other within the amphiphilic molecule. In another example, the "first hydrophilic block" and the "first hydrophobic block" are located at the opposite ends of the amphiphilic molecule in the form of an open chain.

(Amphiphilic Peptide Chain)

In this specification, the term "peptide" refers to a compound formed from two or more amino acids bound together by a peptide bond. In this specification, the term "amino acid" is a concept that includes natural amino acids, unnatural amino acids, and derivatives thereof resulting from modification and/or chemical change. The concept also includes α-amino acids, β-amino acids, γ-amino acids, and the like. The amino acid is preferably an α-amino acid. In the present invention, the term "amphiphilic peptide chain" is a peptide-based amphiphilic molecule, which may partially contain a constituent other than peptide. Examples of such a constituent include modification at N-terminus or C-terminus and non-peptide linker between blocks.

The term "hydrophilic peptide block" refers to a region that shows hydrophilicity, and may partially contain a constituent other than peptide. There is no particular limitation on the degree of the physical property "hydrophilic" of the hydrophilic peptide block. The hydrophilic peptide block needs only be hydrophilic to the extent that the hydrophilic peptide block is more hydrophilic than other regions of an amphiphilic peptide chain and that the amphiphilic peptide chain, constituted by the hydrophilic peptide block and the other regions, as a whole can be amphiphilic. Alternatively, the hydrophilic peptide block needs only be hydrophilic to the extent that the amphiphilic peptide chains are capable of becoming self-organized and forming a self-assembly in a medium.

The amino acids included in the hydrophilic peptide block are not limited to a particular kind. Examples of the amino acids included in the hydrophilic peptide block include N-methylglycine (sarcosine), lysine, and histidine. The "hydrophilicity" may be achieved by, for example, hydrogen bonds formed by side chains of the amino acids included in the hydrophilic peptide block, or may be achieved by hydrogen bonds formed by carbonyl of the main chains of the amino acids included in the hydrophilic peptide block. The amino acids included in the hydrophilic peptide block are preferably nonionic (uncharged) amino acids. The hydrophilicity obtained by hydration is advantageous in that this makes it easy to control the shape of a self-assembly by selecting the length of the hydrophilic peptide block, because the hydrophilicity obtained by hydration is weaker than that obtained by ions. The hydrophilicity obtained by hydration is advantageous also in that the surface of a nanostructure is covered with a nonionic polymer and thereby the nanostructure is not easily recognized as foreign in vivo. A preferred one of such nonionic amino acids is sarcosine.

The hydrophilic peptide block may include amino acids of two or more kinds. The kinds and proportions of the amino acids included in the hydrophilic peptide block are selected appropriately by a person skilled in the art so that the hydrophilic peptide block as a whole is hydrophilic.

The number of the amino acids included in the hydrophilic peptide block is not particularly limited, and is preferably 5 to 80, more preferably 15 to 40, even more preferably 20 to 35, and, in one example, particularly preferably 26. In a case where the number of the amino acids is 5 or more, the hydrophilic peptide block is hydrophilic enough and a self-assembly can easily form a desired shape. In a case where the number of the amino acids is equal to or less than 80, the hydrophilic block does not become too large and a self-assembly can easily form a desired shape.

The term "hydrophobic peptide block" refers to a region that shows hydrophobicity, and may partially contain a constituent other than peptide. There is no particular limitation on the degree of the physical property "hydrophobic" of the hydrophobic peptide block. The hydrophobic peptide block needs only be hydrophobic to the extent that the hydrophobic peptide block is more hydrophobic than other regions of an amphiphilic peptide chain and that the amphiphilic peptide chain, constituted by the hydrophobic peptide block and the other regions, as a whole can be amphiphilic. Alternatively, the hydrophobic peptide block needs only be hydrophobic to the extent that the amphiphilic peptide chains are capable of becoming self-organized and forming a self-assembly in a medium.

The amino acids included in the hydrophobic peptide block are not limited to a particular kind, and are preferably hydrophobic amino acids. Examples of the amino acids included in the hydrophobic peptide block include glycine, alanine, valine, leucine, isoleucine, proline, methionine, tyrosine, tryptophan, aminoisobutyric acid, norleucine, α-aminobutyric acid, and cyclohexylalanine. It is preferable that the hydrophobic peptide block has a helix structure. A hydrophobic peptide block having a helix structure is advantageous in that such blocks are strong in structure and are oriented densely and in parallel. Examples of a hydrophobic peptide block having such a helix structure include poly (leucine-aminoisobutyric acid), polyalanine, polyglycine, and polyproline.

The hydrophobic peptide block may include amino acids of two or more kinds. The kinds and proportions of the amino acids included in the hydrophobic peptide block are selected appropriately by a person skilled in the art so that the hydrophobic peptide block as a whole is hydrophobic.

The number of the amino acids included in the hydrophobic peptide block is not particularly limited, and is preferably 8 to 30, more preferably 8 to 20, even more preferably 12 to 16, and, in one example, particularly preferably 14 or 16.

The ratio in length of the hydrophilic peptide block to the hydrophobic peptide block is not particularly limited. It is preferable that the number of amino acids in the hydrophilic peptide block to that of the hydrophobic peptide block is 1:1 to 3:1.

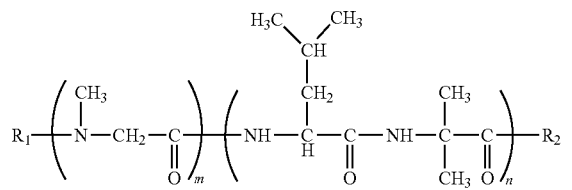

In an even more preferred example, the amphiphilic peptide chain is preferably represented by the following Formula (II), where m and n are as defined in Formula (I).

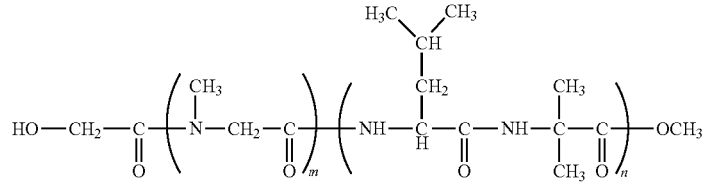

Either of the hydrophilic and hydrophobic peptide blocks can be located on the N-terminus side. In order to achieve easy synthesis, it is preferable that the hydrophilic peptide block is located on the N-terminus side.

The hydrophilic peptide block and the hydrophobic peptide block may be bound together by a linker or may be bound together directly without linkers. The linker may be a linker constituted by peptide or a non-peptide linker.

The N-terminus and C-terminus of the amphiphilic peptide chain are preferably modified (protected) from stability point of view (i.e., in order to obtain a nanostructure whose molecules are not changed by pH, temperature, and/or the like conditions and which is stable to external environment changes). The N-terminus or C-terminus of the amphiphilic peptide chain may be labeled with a fluorescent material or the like which is bound to the terminus.

In one preferred example, the hydrophilic peptide block of the amphiphilic peptide chain contains sarcosine as repeating unit, and the hydrophobic peptide block contains (leucine-aminoisobutyric acid) as repeating unit. In a more preferred example, the amphiphilic peptide chain is preferably represented by the following Formula (I). In Formula (I), m is not particularly limited and is preferably 5 to 80, more preferably 15 to 40, even more preferably 20 to 35 (may be 20 to 30, 22 to 28, 24 to 28, or the like) and, in a particularly preferred example, 26. In Formula (I), n is not particularly limited and is preferably 4 to 15, more preferably 4 to 10, even more preferably 6 to 8 and, in a particularly preferred example, 7 or 8. The poly(leucine-aminoisobutyric acid) of the hydrophobic peptide block forms a helix structure in a case where leucines have structures with the same chirality. In one example, each leucine is L-leucine. In Formula (I), $R_1$ is not particularly limited and is, for example, a non-reactive protecting group, specifically ketole group, acetyl group, or the like. $R_2$ is not particularly limited and is, for example, a non-reactive protecting group, specifically an alkoxy group (e.g., C1-C4 alkoxy group), benzyl ester group, or the like.

Examples of the amphiphilic peptide chain include poly(sarcosine)$_{26}$-b-(L-Leu-Aib)$_7$ (A in FIG. 1), poly(sarcosine)$_{26}$-b-(L-Leu-Aib)$_8$ (S26L16), and the like.

A method of synthesizing an amphiphilic peptide chain is not particularly limited and may be a known peptide synthesis method. The peptide synthesis can be carried out by, for example, peptide condensation using a liquid phase method, or the like.

In a case where a first wall (first region) of the wall of a nanostructure includes amphiphilic peptide chains, the amphiphilic peptide chains may be of the same kind or of different kinds.

(Second Amphiphilic Molecule)

A second amphiphilic molecule refers to an amphiphilic molecule which is different from the first amphiphilic molecule, and is, for example, a lipid molecule or the like. In the following descriptions, a hydrophilic block included in a second amphiphilic molecule may be referred to as "second hydrophilic block", and a hydrophobic block included in the second amphiphilic molecule may be referred to as "second hydrophobic block".

The term "second hydrophilic block" refers to a region that shows hydrophilicity. There is no particular limitation on the degree of the physical property "hydrophilic" of the second hydrophilic block. The second hydrophilic block needs only be hydrophilic to the extent that the second hydrophilic block is more hydrophilic than other regions of a second amphiphilic molecule and that the second amphiphilic molecule, constituted by the second hydrophilic block and the other regions, as a whole can be amphiphilic. Alternatively, the second hydrophilic block needs only be hydrophilic to the extent that the second amphiphilic molecules are capable of becoming self-organized and forming a self-assembly in a medium.

The kinds of constituents of the second hydrophilic block are not particularly limited. Examples of the constituents of the second hydrophilic block include phosphate group, amine group, hydroxyl group, carboxyl group, sulfate group, nitro group, and the like. These hydrophilic functional groups, for example, may constitute a part or an entirety of a chain (for example, these hydrophilic functional groups may be used to bond with other functional groups), or may be located on some other chemical structure (non-limiting examples of the chemical structure include open-chain or cyclic hydrocarbon groups, open-chain or cyclic ether groups, and the like).

The term "second hydrophobic block" refers to a region that shows hydrophobicity. There is no particular limitation on the degree of the physical property "hydrophobic" of the second hydrophobic block. The second hydrophobic block needs only be hydrophobic to the extent that the second hydrophobic block is more hydrophobic than other regions of a second amphiphilic molecule and that the second amphiphilic molecule, constituted by the second hydrophobic block and the other regions, as a whole can be amphiphilic. Alternatively, the second hydrophobic block needs only be hydrophobic to the extent that the second amphiphilic molecules are capable of becoming self-organized and forming a self-assembly in a medium.

The kinds of constituents of the second hydrophobic block are not particularly limited. Examples of the constituents of the second hydrophobic block include: medium-chain hydrocarbon groups; long-chain hydrocarbon groups; medium-chain hydrocarbon groups having one or more substituents selected from aromatic groups, alicyclic groups, and heterocyclic groups; long-chain hydrocarbon groups having one or more substituents selected from aromatic groups, alicyclic groups, and heterocyclic groups; and the like. The medium-chain hydrocarbon groups or long-chain hydrocarbon groups may be saturated or unsaturated. The second amphiphilic molecule may contain, as a second hydrophobic block, only a single medium-chain hydrocarbon group or a single long-chain hydrocarbon group (e.g., single strand lipid molecule). Alternatively, the second amphiphilic molecule may contain, as a second hydrophobic block, a plurality of medium-chain hydrocarbon groups or a plurality of long-chain hydrocarbon groups (e.g., double strand lipid molecule). The second hydrophobic block is selected appropriately according to the type of the first amphiphilic molecule. There is no particular limitation on a lipid for use in one or more embodiments of the present invention.

The number of carbon atoms included in a medium-chain hydrocarbon group or a long-chain hydrocarbon group is not particularly limited, and is preferably not less than 5, more preferably not less than 10, even more preferably not less than 12. The number of carbon atoms included in a medium-chain hydrocarbon group or a long-chain hydrocarbon group may be preferably not more than 20, may be more preferably not more than 18. In one example, the number of carbon atoms included in a medium-chain hydrocarbon group or a long-chain hydrocarbon group is particularly preferably 12, 14, or 16. The length of a long-chain hydrocarbon group affects phase transition temperature; therefore, the length is selected appropriately according to a phase transition temperature of a desired hollow body.

The ratio of the number of atoms in the second hydrophilic block to the number of atoms in the second hydrophobic block is preferably 1:3 to 1:5.

In one example, the "second hydrophilic block" and the "second hydrophobic block" are adjacent to each other within the amphiphilic molecule. In another example, the "second hydrophilic block" and the "second hydrophobic block" are located at the opposite ends of the amphiphilic molecule in the form of an open chain.

(Lipid)

In this specification, the term "lipid" refers to a fatty acid derivative whose amphiphilic molecules are, when in an aqueous medium, arranged such that their second hydrophilic blocks are oriented outward (oriented at aqueous phase) and their second hydrophobic blocks are oriented inward and can thereby form a layer(s) (in a typical example, lipid bilayer). The scope of the meaning of the term "lipid" includes not only natural lipids but also artificial lipids.

Examples of a lipid include phospholipids. Examples of phospholipids include 1,2-dimyristoyl-sn-glycero-3-phosphocholine (DMPC (A in FIG. 1)), 1,2-dipalmitoyl-sn-glycero-3-phosphocholine (DPPC), 1,2-distearoyl-sn-glycero-3-phosphocholine (DSPC), 1,2-dilauroyl-sn-glycero-3-phosphocholine (DLPC), 1,2-dioleoyl-sn-glycero-3-phosphocholine (DOPC), and the like.

In a case where a second wall (second region) of the wall of a nanostructure includes lipid molecules, the molecules may be of a single kind of lipid or of two or more kinds of lipid.

(Hollow Body)

A nanostructure of an embodiment of the present invention is a hollow body constituted by a wall that includes (i) a first wall (first region of the wall) formed from an assembly of a plurality of first amphiphilic molecules (e.g., amphiphilic peptide chains) and (ii) a second wall (second region of the wall) formed from an assembly of a plurality of second amphiphilic molecules (e.g., lipid molecules). There is no particular limitation on how the first amphiphilic molecules (e.g., amphiphilic peptide chains) are assembled and how the second amphiphilic molecules (e.g., lipid molecules) are assembled, and, in one example, the amphiphilic molecules are oriented and associated together in a self-assembled manner. In a more specific example, the amphiphilic molecules are assembled by hydrophobic interaction.

The following description is based on the assumption that, for example, the first amphiphilic molecules are amphiphilic peptide chains and the second amphiphilic molecules are lipid molecules.

A first wall may have a layered structure. For example, the following structure can be employed: hydrophilic peptide blocks are arranged to form inner and outer surface layers of the first wall; and hydrophobic peptide blocks are arranged to form an internal layer of the first wall. More specifically, the first wall of the hollow body can be an association of amphiphilic peptide chains arranged such that adjacent amphiphilic peptide chains have their hydrophilic peptide blocks located at opposite ends. As such, the first wall can have a three-layer structure consisting of: a first hydrophilic layer constituted by hydrophilic peptide blocks of some amphiphilic peptide chains; a hydrophobic layer constituted by hydrophobic peptide blocks; and a second hydrophilic layer constituted by hydrophilic peptide blocks of the other amphiphilic peptide chains.

A second wall may have a layered structure. For example, the following structure can be employed: second hydrophilic blocks are arranged to form inner and outer surface layers of the second wall; and second hydrophobic blocks are arranged to form an internal layer of the second wall. More specifically, the second wall of the hollow body can form a lipid bilayer structure.

In a case where the first wall and the second wall are structured like above, the outer surface layer of the hollow body is hydrophilic and therefore has good affinity with water. This achieves better adaptability in vivo. Furthermore, since the inner surface layer of the hollow body is hydrophilic, it is possible to suitably retain (preferably encapsulate) a hydrophilic agent. Moreover, at temperatures below the phase transition temperature at which the second wall of the nanostructure transitions from its solid phase to its liquid phase (liquid state that includes liquid crystalline state), it possible to prevent or reduce the leakage of the retained agent, due to hydrophobic interactions between the hydrophobic layer of the amphiphilic peptide chains and the hydrophobic layer of lipid molecules.

A hollow body is structured such that an assembly of a plurality of amphiphilic peptide chains forms a first wall and that an assembly of a plurality of lipid molecules forms a second wall. The hollow body, which has the first wall and the second wall, thereby shows a phase transition temperature that is higher than the phase transition temperature of the second wall. The hollow body has structural stability resulting from the hardness of the first wall, and has temperature responsivity resulting from the properties of the second wall being in its solid phase at low temperatures and being in its liquid phase at high temperatures. With regard to the structural stability, for example, if the hollow body maintains its structure even after at least one month preservation at 4° C., the hollow body can be said to have sufficient structural stability.

As illustrated in B of FIG. 1, the hollow body is structured such that the first wall(s) (peptide membrane) and the second wall(s) (lipid domain (lipid gate)) are separated by phase separation. That is, the structure of the hollow body is not a uniform mixture of amphiphilic peptide chains and lipid molecules. The hollow body has such a structure in which the first wall(s) and the second wall(s) are separated by phase separation, and is thereby capable of ensuring a sufficient size of a gate(s) that opens at and above the phase transition temperature of the second wall. This makes it possible, in a case where the hollow body encapsulates an agent therein, to release, through the gate(s), the agent that is smaller in size than the gate(s) at and above the phase transition temperature of the second wall.

The number of first walls and the number of second walls of the hollow body are not particularly limited, provided that each number is at least one. The hollow body may have a plurality of first walls and/or a plurality of second walls. In one example, on the outer surface of the hollow body, a second wall which is a region in the form of an island is surrounded by a first wall, or a plurality of second walls which are regions in the form of islands are distributed and surrounded by a first wall. In such cases, the outer surface of the hollow body is constituted by: a single continuous first wall; and one second wall in the form of an island or two or more second walls in the form of islands distributed within the first wall. The shape of the second wall(s) at the outer surface of the hollow body is not particularly limited. In one example, the shape is a circle or an oval. At and above the phase transition temperature of the second wall, the gate(s) corresponding to the shape(s) of the second wall(s) at the outer surface can open.

With regard to the hollow body, the ratio of the surface area occupied by the first amphiphilic molecules (i.e., occupied surface area of the first amphiphilic molecules) to that by the second amphiphilic molecules is not particularly limited, and is, for example, preferably 40:60 to 95:5, more preferably 69:31 to 90:10. The molar ratio of the first amphiphilic molecules to the second amphiphilic molecules is selected appropriately according to the type of first amphiphilic molecule and the type of second amphiphilic molecule.

In the present embodiment, the shape of the hollow body is not particularly limited. In order to achieve easy cellular uptake, it is preferable that the hollow body has a spherical shape. In order to better retain the agent, it is preferable that the hollow body has a closed structure (i.e., a structure with no openings) at temperatures below the phase transition temperature at which the second wall transitions from its solid phase to its liquid phase.

The size of the hollow body is not particularly limited. In order to achieve a suitable size for use in vivo, for example, the average hydrodynamic diameter of hollow bodies is preferably 10 to 500 nm, more preferably 30 to 250 nm, even more preferably 50 to 100 nm. The average hydrodynamic diameter is the average of hydrodynamic diameters of hollow bodies in 150 mM NaCl physiological saline having a pH of 7.4 measured by dynamic light scattering at 25° C.

The thickness of the first wall of the hollow body can depend on the length of each amphiphilic peptide chain, and can be, for example, 2 to 10 nm. The thickness of the second wall of the hollow body can depend on the length of each lipid molecule, and can be, for example, 3 to 7 nm.

In one example, the hollow body has a closed structure at temperatures below the phase transition temperature. At and above the phase transition temperature, the hollow body has a structure in which a gate(s) at the second wall(s) is open because the second wall(s), which is formed from an assembly of a plurality of lipid molecules, is in its liquid phase. With regard to the hollow body, the phase transition temperature at which the second wall transitions from its solid phase to its liquid phase is 30 to 40° C. At such phase transition temperature, the first wall(s) is in its solid phase. A method of warming the hollow body to a temperature equal to or above the phase transition temperature of the second wall(s) and thereby bringing the hollow body into a state in which the gate(s) is open in vivo is, for example, as follows. By using the hollow body in combination with a molecule that has the function of generating heat upon irradiation with light (e.g., infrared light) and thereby warming its surroundings, it is possible to increase the temperature of the hollow body to a temperature equal to or above the phase transition temperature. Furthermore, upon reaching an inflamed site having a temperature equal to or above the phase transition temperature of the second wall(s), the hollow body will have a temperature equal to or above the phase transition temperature.

As described earlier, in one example, the first wall(s) is in its solid phase at the phase transition temperature at which the second wall(s) transitions from its solid phase to its liquid phase. In other words, the phase transition temperature of the first wall(s), at which the first wall(s) transitions from its solid phase to its liquid phase, is higher than the phase transition temperature of the second wall(s), at which the second wall(s) transitions from its solid phase to its liquid phase. For example, the phase transition temperature of the first wall(s), at which the first wall(s) transitions from its solid phase to its liquid phase, is 10° C. or more higher, preferably 20° C. more higher, than the phase transition temperature of the second wall(s), at which the second wall(s) transitions from its solid phase to its liquid phase.

Figure 2:
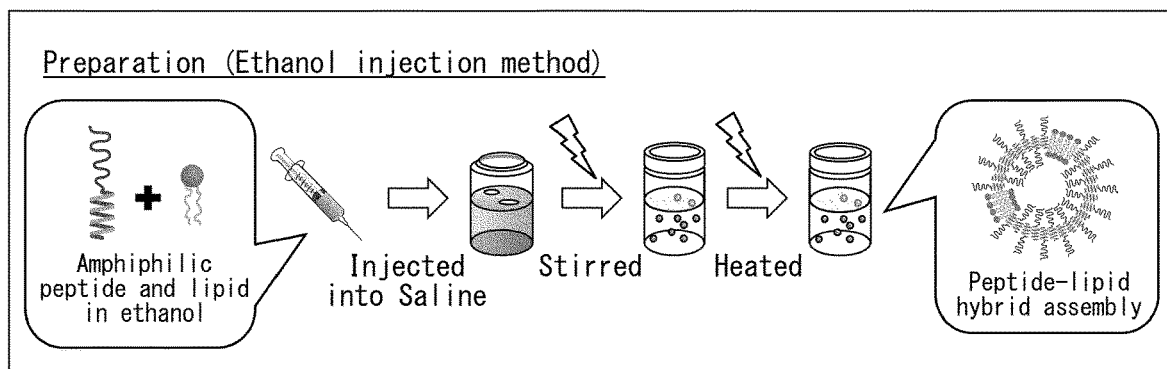
FIG. 2 schematically illustrates an example of a method of producing a nanostructure.

A hollow body is prepared by heating an aqueous medium that contains first amphiphilic molecules (e.g., amphiphilic peptide chains) and second amphiphilic molecules (e.g., lipid molecules). The hollow body can be prepared by, for example, dispersing amphiphilic peptide chains and lipid molecules into an aqueous medium to obtain a dispersion and then heating the dispersion (see FIG. 2). With this, the amphiphilic peptide chains and lipid molecules associate together to form spherical shapes. Such an obtained spherical shape has a structure in which the first wall(s) and the second wall(s) are separated by phase separation, as described earlier.

Alternatively, a hollow body may be prepared by (i) dispersing first amphiphilic molecules (e.g., amphiphilic peptide chains) and second amphiphilic molecules (e.g., lipid molecules) in a pre-heated aqueous medium and (ii) continuing heating for a predetermined period of time.

In this specification, the term "aqueous medium" refers to a liquid whose main component is water. In this specification, the term "liquid whose main component is water" means that the percentage of the volume of water occupying the liquid is greater than other components, and means that preferably more than 50% but not more than 100% of the total volume of the liquid is water. The aqueous medium is preferably a liquid that is safe for use in vivo, such as physiological saline or distilled water for injection, as well as pH buffer solution or the like.

The amphiphilic peptide chains may be dissolved in an organic solvent (ethanol, dimethylformamide, methanol or the like) to obtain a solution first and then the solution may be added (for example, injected) to the aqueous medium. The organic solvent is preferably a liquid that is safe for use in vivo, and is more preferably ethanol. By dissolving the amphiphilic peptide chains in an organic solvent first, the amphiphilic peptide chains which are dissociated from each other, not in the crystal form, are added into the aqueous medium, and therefore it is possible to allow the amphiphilic peptide chains to form a hollow body efficiently. Thus, in one example, the "aqueous medium" can contain such an organic solvent.

In preparation of a hollow body, the amount of amphiphilic peptide chains and lipid molecules relative to the aqueous medium is not particularly limited, and is, for example, preferably 0.001 to 100 mg/mL, more preferably 0.01 to 10 mg/mL, in view of dispersibility in water. The amount of amphiphilic peptide chains is not particularly limited, and is, for example, preferably more than 0.5 mol and less than 12 mol relative to 1 mol of lipid molecules, more preferably not less than 1 mol and not more than 4 mol relative to 1 mol of lipid molecules, in order to achieve higher yield.

In a case where an aqueous medium is not preheated to any of the following heating temperatures, the amphiphilic peptide chains and lipid molecules are dispersed in the aqueous medium at preferably 4 to 30° C. The temperature at which the amphiphilic peptide chains and lipid molecules are dispersed in the aqueous medium may be selected appropriately according to the phase transition temperature at which the lipid transitions from its solid phase to its liquid phase, while ensuring that temperature falls within the above range. For example, in case where the lipid has a high phase transition temperature and does not mix with the aqueous medium and is separated from the aqueous medium at room temperature, the above dispersion is carried out preferably at a temperature above the phase transition temperature of the lipid. In order to uniformly disperse the amphiphilic peptide chains and lipid molecules, it is preferable to carry out stirring.

The heating temperature is not particularly limited and is, for example, preferably 30 to 90° C. The heating time is not particularly limited and is, for example, preferably 10 minutes to 24 hours.

Although the above description dealt with a hollow body having a spherical shape, the shape of the hollow body is not limited to such. The shape of the hollow body may be an oval or the like.

Furthermore, although the above description dealt with an example case in which the first amphiphilic molecules are amphiphilic peptide chains and the second amphiphilic molecules are lipid molecules, other cases may be employed in which the first and second amphiphilic molecules are some other kinds of molecule.

(Retainment of Agent)

A nanostructure in accordance with an embodiment of the present invention retains (preferably encapsulates) an agent. In this specification, the phrase "encapsulate an agent therein" means that an agent is not covalently bonded to a hollow body and that the agent is present in an inner space defined by the hollow body. Typically, an agent, which is dissolved or suspended in a liquid, is encapsulated. The liquid can be a hydrophilic liquid, and can be the foregoing aqueous medium.

A method of allowing a hollow body to retain (preferably encapsulate) an agent is not particularly limited. In one preferred example, a hollow body is allowed to form in a liquid (solution or suspension) containing an agent. For example, first and second amphiphilic molecules (e.g., amphiphilic peptide chains and lipid molecules) are dispersed in an aqueous medium containing an agent and then heated to prepare a hollow body. Alternatively, a hollow body may be prepared by (i) dispersing an agent, first amphiphilic molecules (e.g., amphiphilic peptide chains), and second amphiphilic molecules (e.g., lipid molecules) in a pre-heated aqueous medium and (ii) continuing heating for a predetermined period of time.

That is, in one example, a method of producing a nanostructure of the present embodiment includes a step of preparing a hollow body while allowing the hollow body to retain an agent by heating an aqueous medium that contains the agent, first amphiphilic molecules (e.g., amphiphilic peptide chains), and second amphiphilic molecules (e.g., lipid molecules). This method makes it possible to allow an agent to be efficiently and easily retained (preferably encapsulated).

The size of the agent is not particularly limited, provided that the size of the agent is smaller than the inner diameter of the hollow body. The size of the agent is preferably equal to or less than 50 nm, more preferably equal to or less than 20 nm. In one example, the molecular weight of the agent is equal to or less than 100000, preferably equal to or less than 50000, more preferably equal to or less than 10000.

In one example, the agent is hydrophilic. The term "hydrophilic agent" also includes hydrophobic agents whose surface has been treated to be hydrophilic.

Examples of the agent include effective ingredients of pharmaceuticals and food (in particular, functional food), effective ingredients in the field of cosmetics, molecular probes for imaging systems, and various research reagents. The agent can be an organic compound, inorganic compound, biomolecule such as protein or nucleic acid, or the like. A single kind of agent may be encapsulated in the nanostructure or two or more kinds of agent may be encapsulated in the nanostructure. It should be noted that the nanostructure of the present embodiment excludes those in which the encapsulated agent is in the form of saline solution (e.g., physiological saline) (that is, the agent itself is saline solution or the agent is sodium chloride dissolved in water in liquid form) and the nanostructure does not contain components other than the agent (saline solution). The nanostructure of the present embodiment enables efficient cellular uptake of a drug which alone had not been taken up by cells or a drug which alone had been difficult to be taken up by cells.

The nanostructure of the present embodiment contains peptide within its structure and thus is biodegradable. Therefore, the nanostructure may be biodegraded in a living organism (for example, cell) and the agent may be released in the living organism (for example, cell). In one example, the release of the agent can continue, for example, for 1 day or more, 2 days or more, or 4 days or more. The biodegradation can take place due to, for example, protease such as proteinase or peptidase.

The nanostructure of the present embodiment can be taken up through endocytosis mediated by clathrin in an energy dependent manner (note, however, that this does not imply any limitation). Clathrin is a protein that many biological species have, and therefore the nanostructure of the present embodiment can be used in cells of many biological species.

According to the nanostructure of the present embodiment, by changing the kinds of first and second amphiphilic molecules (e.g., amphiphilic peptide chains and lipid molecules), it is possible to adjust the structural stability, temperature responsivity, size, shape, tissue selectivity, and rate of decomposition in vivo of the nanostructure, release characteristics (controlled release property or the like) of the encapsulated agent, and/or the like.

(Other Applications)

The present embodiment also provides a pharmaceutical composition containing a nanostructure. The pharmaceutical composition contains a medicament as the agent. Any medicament can be used without particular limitation according to a target disease. Specific examples of the medicament include anticancer agents, antibacterial agents, antiviral agents, anti-inflammatory agents, immunosuppressive agents, steroids, hormones, and anti-angiogenic agents.

The route of administration of the pharmaceutical composition is not particularly limited. The pharmaceutical composition may be administered systemically by oral administration, intravascular administration such as intravenous administration or intraarterial administration, enteral administration, or the like, or may be administered topically by transdermal administration, sublingual administration, or the like. In one example, the pharmaceutical composition is preferably administered by intravenous injection. The dose of the pharmaceutical composition of the present embodiment administered to a patient may be selected appropriately according to the kind of the encapsulated medicament, age, gender, body weight, and condition of the patient, route of administration, frequency of administration, administration period, and the like. A target organism that receives the administration is not particularly limited as well. Examples include plants and animals. Animals such as fishes, amphibians, reptiles, birds, and mammals are preferred, and mammals are more preferred. Mammals are not limited to a particular kind, and examples include: laboratory animals such as mice, rats, rabbits, guinea pigs, and non-human primates; pets such as dogs and cats; domestic animals such as cattle, horses, and pigs; and humans.

The dosage form of the pharmaceutical composition is not particularly limited, and can be a solution obtained by dispersing a nanostructure in a hydrophilic liquid. Examples of the hydrophilic liquid include water, alcohols, and buffer solutions. The pharmaceutical composition may further contain a preservative, a stabilizer, a buffer agent, an osmotic adjuster, a colorant, a flavoring agent, a sweetener, an antioxidant, a viscosity modifier, and/or the like, in addition to the nanostructure.

The nanostructure of the present embodiment encapsulates an agent therein, is easily taken up by cells, and can release the agent (for example, release in a controlled manner) in the cells. As such, the pharmaceutical composition of the present embodiment is capable of efficiently delivering a medicament into cells as compared to cases in which the pharmaceutical composition is administered alone. Thus, lower doses can be enough to provide the effect of the medicament for long time.

(Recap)

Aspects of the present invention can also be expressed as follows.

(1)

A nanostructure which is a hollow body constituted by a wall, the wall including a first region and a second region, the first region being formed from an assembly of a plurality of first amphiphilic molecules containing a hydrophilic block and a hydrophobic block, the second region being formed from an assembly of a plurality of second amphiphilic molecules which are different from the first amphiphilic molecules, the first region being arranged to be in its solid phase at a phase transition temperature at which the second region of the wall transitions from its solid phase to its liquid phase.

(2)

A nanostructure which is a hollow body constituted by a wall, the wall including a first region and a second region, the first region being formed from an assembly of a plurality of first amphiphilic molecules containing a hydrophilic block and a hydrophobic block, the second region being formed from an assembly of a plurality of second amphiphilic molecules which are different from the first amphiphilic molecules, the first amphiphilic molecules being amphiphilic peptide chains containing a hydrophilic peptide block and a hydrophobic peptide block, the second amphiphilic molecules being lipid molecules.

(3)

The nanostructure as set forth in (1), in which the second amphiphilic molecules are lipid molecules.

(4)

The nanostructure as set forth in (3), in which the second amphiphilic molecules are phospholipid molecules.

(5)

The nanostructure as set forth in (1), (3), or (4), in which the first amphiphilic molecules are amphiphilic peptide chains containing a hydrophilic peptide block and a hydrophobic peptide block.

(6)

The nanostructure as set form in (5), in which the hydrophobic peptide block has a helix structure.

(7)

The nanostructure as set forth in any one of (1) to (6), in which an average hydrodynamic diameter, measured by dynamic light scattering at 25° C. in 150 mM NaCl physiological saline having a pH of 7.4, is 10 to 500 nm.

(8)

The nanostructure as set forth in any of (1) to (7), in which a ratio of an occupied surface area of the first amphiphilic molecules to an occupied surface area of the second amphiphilic molecules is 40:60 to 95:5.

(9)

The nanostructure as set forth in any of (1) to (8), in which the nanostructure has an agent retained therein.

(10)

A pharmaceutical composition containing a nanostructure recited in (9).

(11)

A method of producing a nanostructure recited in any of (1) to (10), the method including a step of preparing a hollow body by heating an aqueous medium that contains the first amphiphilic molecules and the second amphiphilic molecules.

The following will provide Examples to more specifically describe embodiments of the present invention. As a matter of course, the present invention is not limited to Examples provided below, but details of the present invention can be realized in various manners. Further, the present invention is not limited to the embodiments described above, and it may be varied in various ways within the scope of the appended claims. Thus, an embodiment based on a combination of technical means disclosed in different embodiments is encompassed in the technical scope of the present invention. Furthermore, all of the publications and patents cited in the present specification are incorporated herein by reference in their entirety.

EXAMPLES

Example 1

Morphology 1 of Peptide-Lipid Hybrid Vesicle (PLHV)

(Sample Preparation)

The amphiphilic polypeptide poly(sarcosine)$_{26}$-b-(L-Leu-Aib)$_7$ (hereinafter may be referred to as "S26L14") and poly(sarcosine)$_{26}$-b-(L-Leu-Aib)$_8$ (S26L16) were synthesized as reported previously in Reference Literatures 1 and 2. The synthesis of S26L14 was confirmed by $^1$H NMR spectroscopy and MALDI-TOF MS spectrometry.

Peptide-lipid hybrid vesicles, peptide assemblies and liposomes were prepared by the ethanol injection method. S26L14 (20 mg) and 1,2-dimyristoyl-sn-glycero-3-phosphocholine (DMPC) (20 mg) were each dissolved in ethanol (400 μL) to obtain stock solutions (1 mg/20 μL). Different formulations were then prepared by mixing the S26L14 stock solution and the DMPC stock solution so that the molar ratio between S26L14 and DMPC would be 0:1, 1:4, 1:2, 1:1, 2:1, 4:1, 12:1, and 1:0. An aliquot (a mixture of S26L14 and DMPC (10 μL), S26L14 only (10 μL), or DMPC only (10 μL)) was added (injected) into physiological saline (150 mM NaCl, pH 7.4, 1 mL) with stirring at 25° C. for 30 minutes, then the stirring was stopped and the dispersion was heated at 90° C. for 1 hour, and air-cooled to room temperature. In this way, the following samples were obtained: samples of S26L14+DMPC in which the S26L14/DMPC molar ratios are 1:4, 1:2, 1:1, 2:1, 4:1, and 12:1; a sample composed only of S26L14: and a sample composed only of DMPC (concentrations are all 0.35 mM). Note that the peptide-lipid hybrid vesicles prepared from S26L14/DMPC mixtures with molar ratios of 1:4, 1:2, 1:1, 2:1, 4:1, and 12:1 are referred to as PLHV1-4, PLHV1-2, PLHV1-1, PLHV2-1, PLHV4-1, and PLHV12-1, respectively.

The same operations as described above were carried out, except that the lipid was changed from DMPC to 1,2-dipalmitoyl-sn-glycero-3-phosphocholine (DPPC) or 1,2-distearoyl-sn-glycero-3-phosphocholine (DSPC). In this way, a sample of S26L14+DPPC in which the S26L14/lipid molar ratio is 1:1 and a sample of S26L14+DSPC in which the S26L14/lipid molar ratio is 1:1 were obtained.

The same operations as described earlier were carried out, except that the amphiphilic polypeptide was changed from S26L14 to S26L16 and that each mixture was injected into saline of 90° C., stirred for 30 minutes, the stirring was stopped, a heat treatment at 90° C. was carried out for 1 hour, and air-cooled to room temperature. In this way, a sample of S26L16+DMPC in which the S26L16/DMPC molar ratio is 1:1, a sample of S26L16+DPPC, and a sample of S26L16+DSPC were obtained.

(Transmission Electron Microscopy (TEM))

TEM images were taken using a JEM-1230 (manufactured by JEOL) at an accelerating voltage of 80 kV. For observations, a drop of dispersion was mounted on a carbon-coated Cu grid (Okenshoji Co., Ltd., Japan) and stained negatively with 2% samarium acetate, followed by removal of the excess fluid with filter paper.

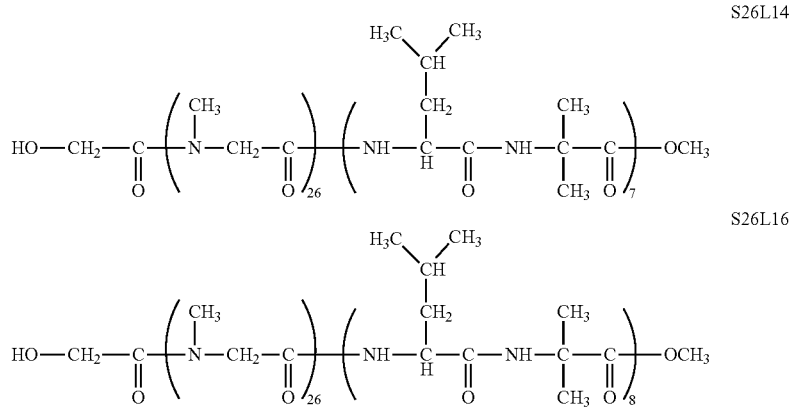

(Dynamic Light Scattering (DLS))

The hydrodynamic diameter of molecular assemblies in physiological saline was analyzed by ELSZ-2PL (Otsuka Electronics, Japan) using a He—Ne laser. Measurements were performed at 25° C.

(Phospholipid Quantitative Determination)

PLHV1-1 dispersion was washed by dialysis to remove free S26L14 and DMPC. After that, S26L14 and DMPC concentrations in PLHV1-1 was estimated from UV absorbance at 220 nm and at 600 nm with using Phospholipid Quantitative Determination Kit (PHOSPHOLIPIDS C AUTOKIT 2-10 DEGC 120TST, Wako, Japan).

(Results and Consideration)

Figure 3:
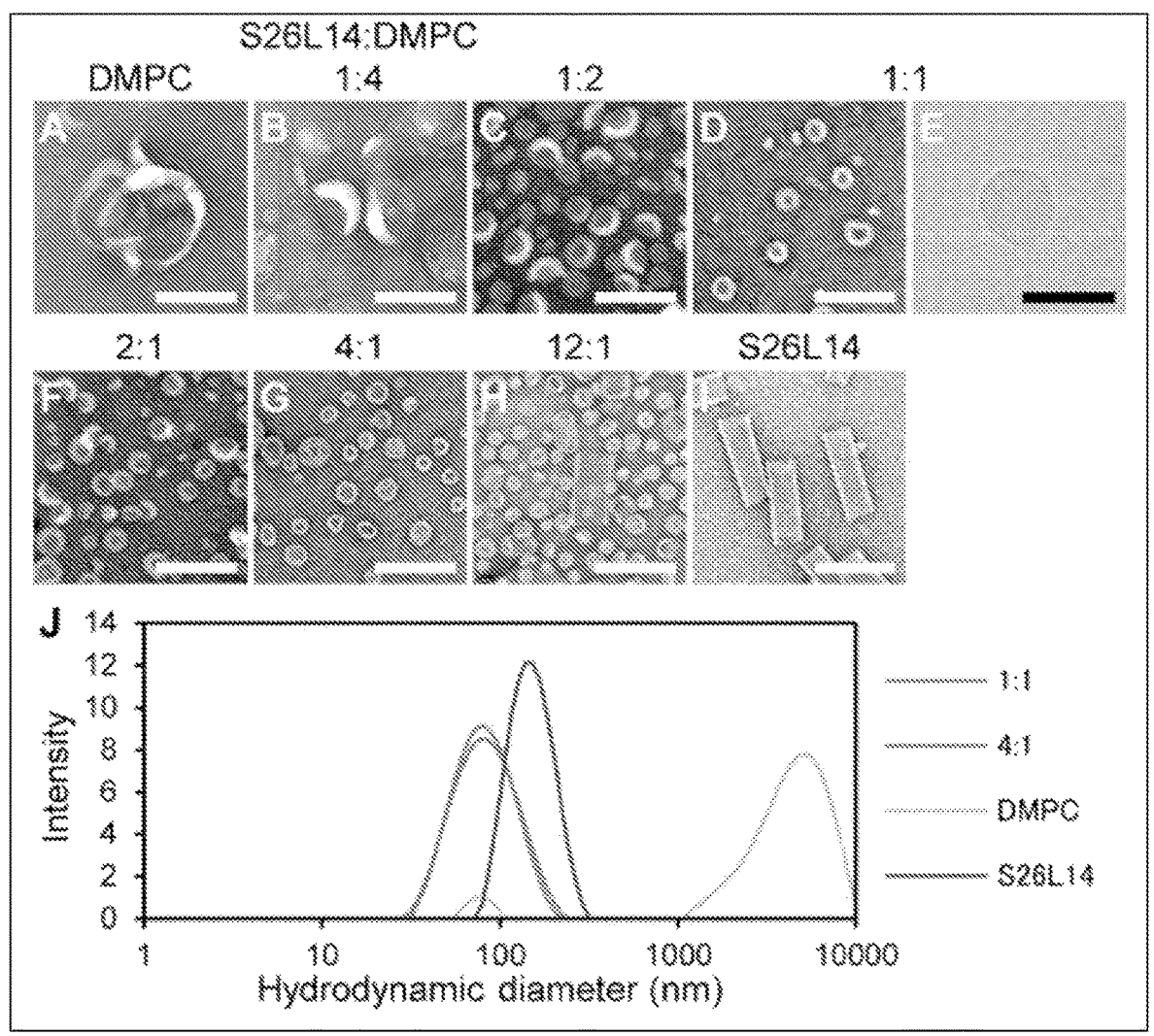
FIG. 3 shows TEM images (A to D, F to I) taken in Example 1, cryo-TEM image (E) taken in Example 1, and the results of DLS analysis (J) in Example 1.
Figure 4:
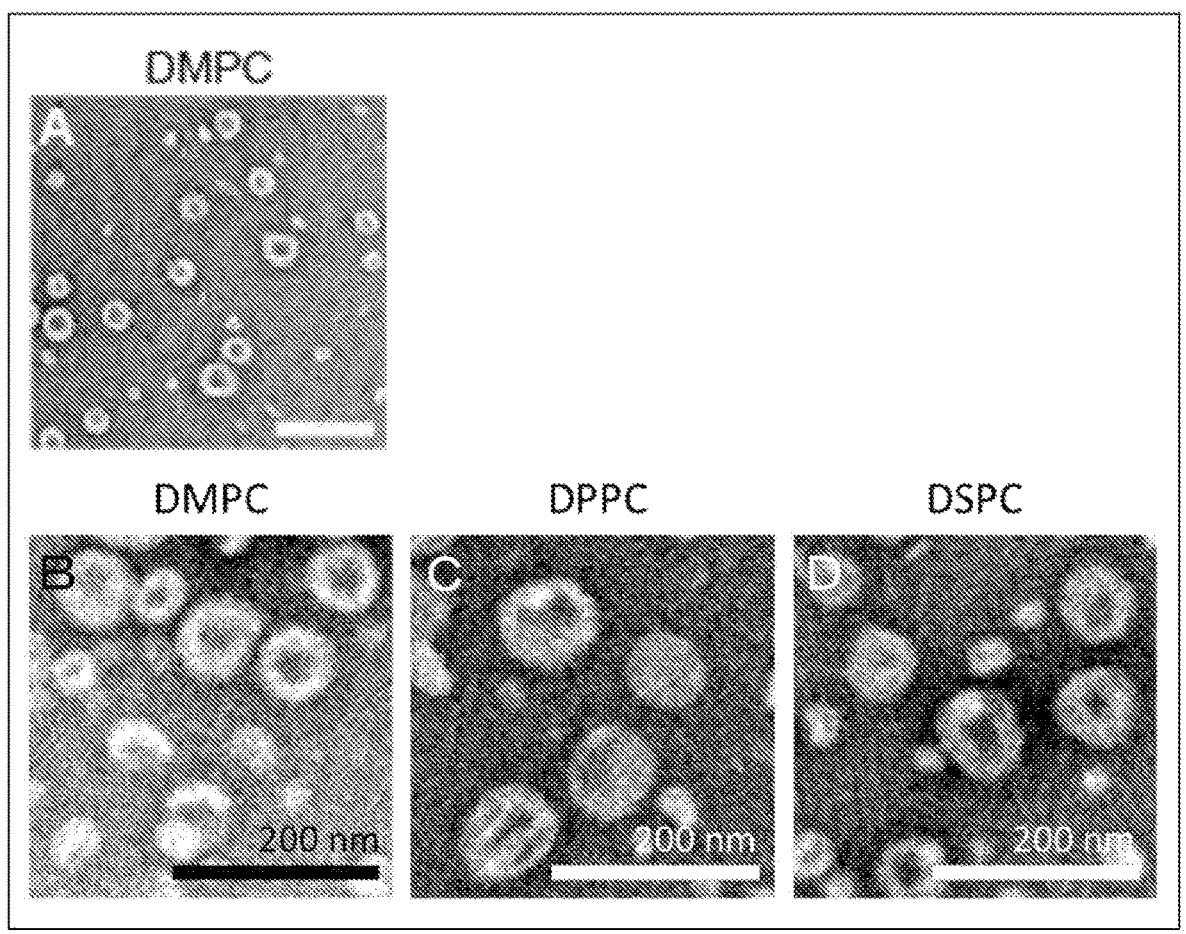
FIG. 4 shows TEM images taken in Example 1.
Figure 5:
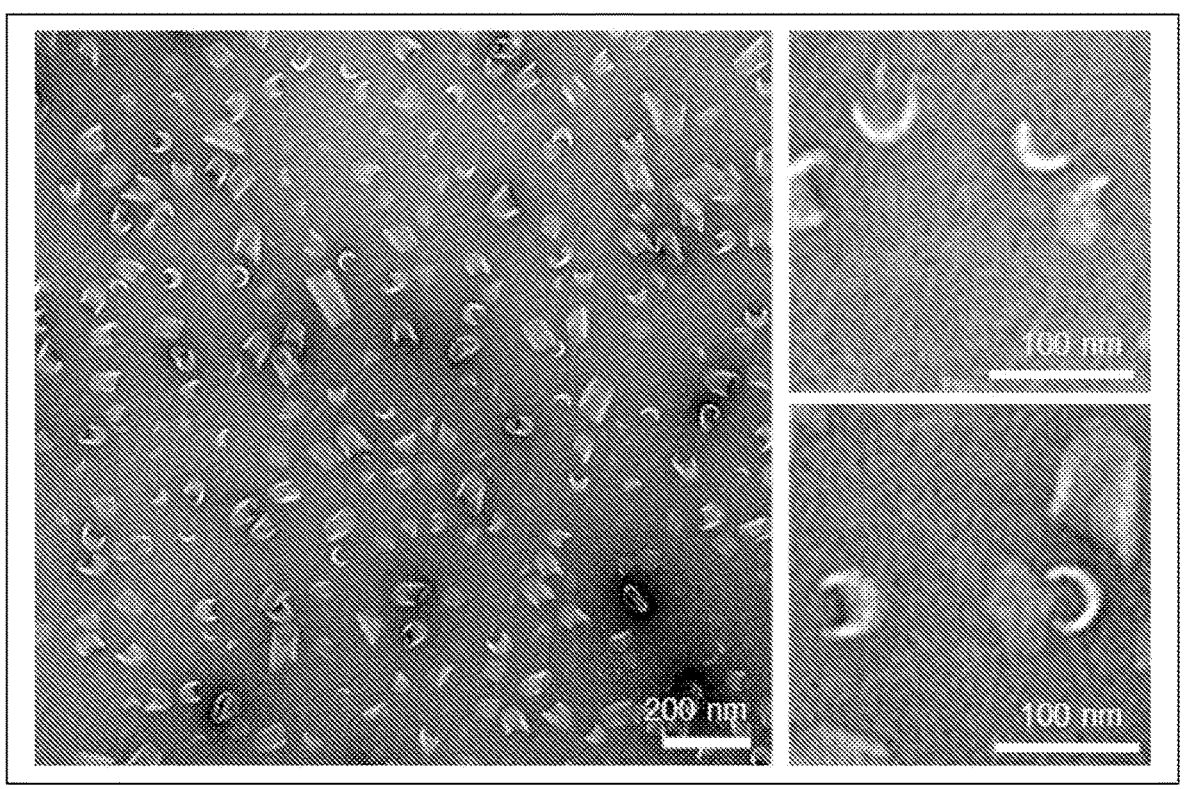
FIG. 5 shows TEM images taken in Example 1.
Figure 6:
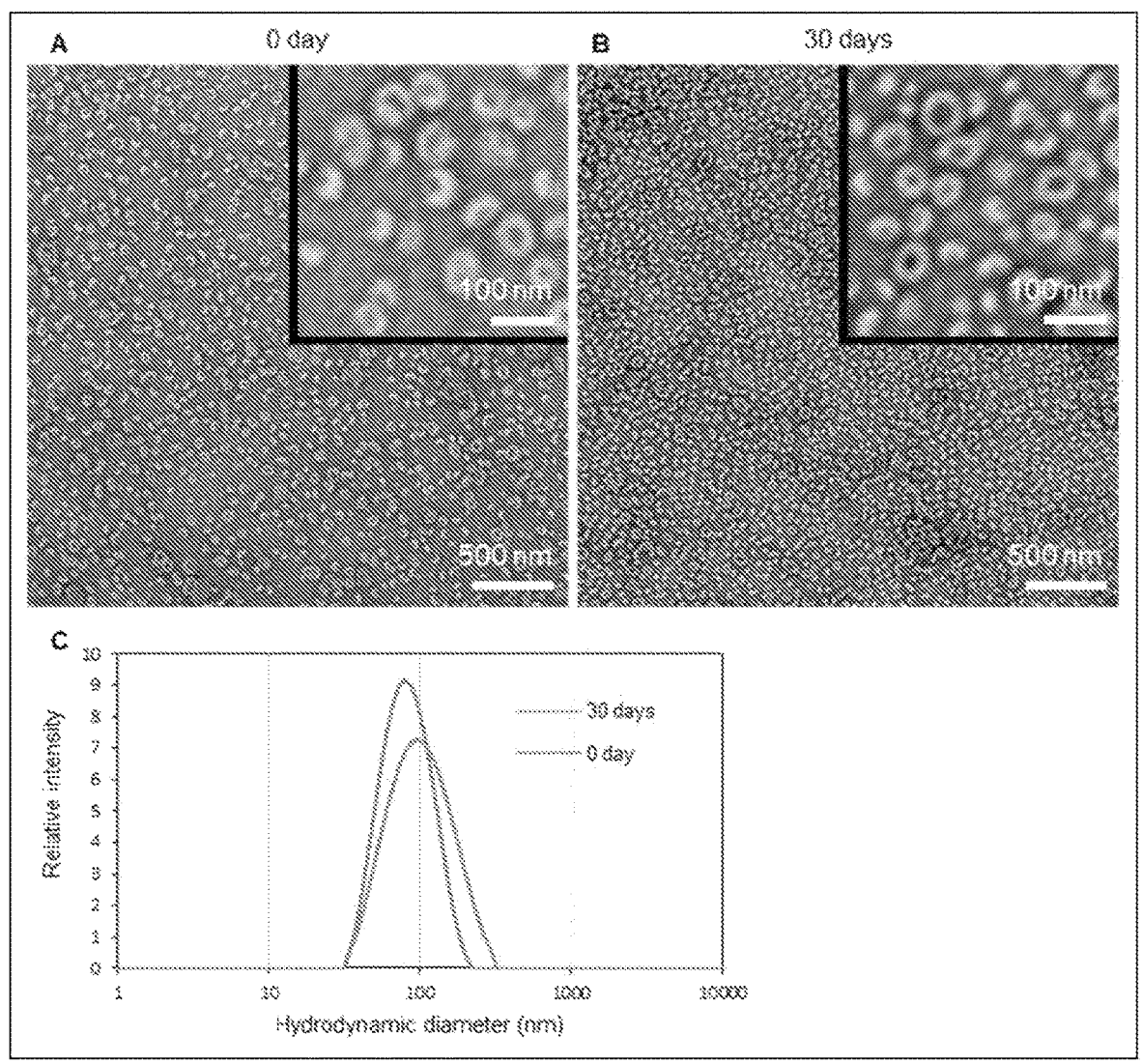
FIG. 6 shows TEM images taken in Example 1 and the results of DLS analysis in Example 1.

A to D and F to I of FIG. 3, A to F of FIG. 4, FIG. 5, and A and B of FIG. 6 show TEM images. The scale bars in A to D and F to I of FIG. 3 and A to C of FIG. 4 each indicate 200 nm. E of FIG. 3 shows a cryo-TEM image. The scale bar in E of FIG. 3 indicates 100 nm. J of FIG. 3, C of FIG. 6, and Table 1 show the results of DLS. Table 2 shows the results of phospholipid quantitative determination.

TABLE 1

DLS Results of Each Assembly and Theoretical Occupied Area of S26L14 and DMPC for Each Assembly

|  | Ratio (%) | $D_H$ (nm) | PDI | Theoretical occupied area ratio (%) | Shape |
| --- | --- | --- | --- | --- | --- |
| DMPC | 0:100 | 2286 | 0.87 | 0:100 | Various sized vesicle |
| PLHV1-4 | 20:80 |  |  | 36:64 | Various sized vesicle |
| PLHV1-2 | 33:67 |  |  | 53:47 | Various sized vesicle |
| PLHV1-1 | 50:50 | 75.5 | 0.11 | 69:31 | Uniform vesicle |
| PLHV2-1 | 67:33 |  |  | 82:18 | Uniform vesicle |
| PLHV4-1 | 80:20 | 76.4 | 0.12 | 90:10 | Uniform vesicle |
| PLHV12-1 | 92:8 |  |  | 96:4 | Uniform Vesicle + Tube |
| S26L14 | 100:0 | 145.1 | 0.10 | 100:0 | Tube |

TABLE 2

Composition ratio of S26L14 and DMPC in PLHV

|  | S26L14 | | | DMPC | | | |
| --- | --- | --- | --- | --- | --- | --- | --- |
|  | $Abs_{220}$ | mg/mL | nmol/mL | $Abs_{600}$ | mg/mL | nmol/mL | S26L14:DMPC |
| PLHV1-1 | 0.113 | 0.196 | 57.8 | 0.052 | 0.035 | 47.8 | 1:0.83 |

The morphology of assemblies prepared from a combination of S26L14 and DMPC at a molar ratio of 1:1, a combination of S26L16 and DMPC at a molar ratio of 1:1, a combination of S26L16 and DPPC at a molar ratio of 1:1, and a combination of S26L16 and DSPC at a molar ratio of 1:1 was observed by transmission electron microscopy (TEM). A vesicular assembly with a uniform diameter of 75 nm was obtained (D of FIG. 3 and A to D of FIG. 4). S26L14 formed a nanotube with a uniform diameter and length of 80 nm and 200 nm, respectively. In contrast, DMPC formed various sized liposomes with diameters of 10 to 10000 nm (A of FIG. 3). The assembly shape of the PLHV was clearly different from those of the pure components. Dynamic light scattering (DLS) analysis also showed different sizes among assemblies (J of FIG. 3 and Table 1); PLHV, S26L14 nanotubes, and DMPC liposomes were 76 nm, 145 nm, and 2286 nm in diameter, respectively. These results indicate that S26L14 and DMPC coassembled to form a hybrid vesicle. The "uniform" size of the PLHVs probably arises from S26L14 forming a curved sheet domain with a uniform curvature (FIG. 5) within a hybrid membrane.

Next, the effect of the mixing ratio of PLHVs was investigated. In S26L14/DMPC ratios of 1:4 and 1:2, a liposome-like hybrid assembly was observed. The sizes of the assemblies were not uniform and ranged from 50 to 2000 nm (B and C of FIG. 3). The membrane thickness of PLHV was the same as that of DMPC liposomes (A of FIG. 3). Molar ratios of 1:1, 2:1, and 4:1 yielded PLHVs with uniform diameters of 75 nm (C to G of FIG. 3). From dynamic light scattering (DLS) measurement, these PLHVs showed a polydispersity index of approximately 0.1 (Table 1). In contrast, a 12:1 mixture showed not only 75 nm-sized hybrid vesicle but also nanotubes in the dispersion (H of FIG. 3). These morphological results are explained by the ratio of calculated occupied surface areas as follows. The occupied surface area of an α-helix block of S26L14 and DMPC is regarded as 1.50 $nm^2$ (Reference Literature 3) and 0.66 $nm^2$ (Reference Literatures 4 and 5), respectively. For the molar ratio of 1:4, the surface area ratio of S26L14: DMPC was 36:64. The contribution from the lipid membrane dominates at this mixing ratio, and a liposome-like assembly was observed. For 1:1, 2:1, and 4:1 molar ratios, the surface area ratios of S26L14:DMPC were 69:31, 82:18, and 90:10, respectively (Table 1). For these ratios, the morphology of the PLHV is dominated by the contribution from S26L14. The composition ratio of S26L14 and DMPC in PLHV1-1 was evaluated after dialysis, which removes free S26L14 and DMPC. The content of S26L14 was estimated by its absorbance at 220 nm, and that of DMPC was determined by using a phospholipid quantitative determination kit, respectively. According to the results, PLHV1-1 was composed of S26L14 and DMPC at a molar ratio of 1:0.83, which is close to the initial mixing ratio of 1:1 (Table 2).

PLHV1-1 vesicles were stored at 4° C. for 1 month, and their structural stability was evaluated by TEM observations and DLS analysis (FIG. 6). The shape of the vesicles was maintained during this period. The polypeptiderich hybrid vesicles showed high stability when compared to that of general liposomes. Thus, these hybrid vesicles have sufficient stability (i.e., at least 1 month) to be used as DDS carriers.

Example 2

Morphology 2 of Peptide-Lipid Hybrid Vesicle (PLHV)

(Circular Dichroism (CD))

CD measurements were carried out on a JASCO J-720 (manufactured by JEOL) using a cell with an optical path length of 1 cm. Data was recorded at 25° C. 0.35 mM dispersion was diluted five-fold before CD data collection, and used as a measurement sample.

(Results and Consideration)

Figure 7:
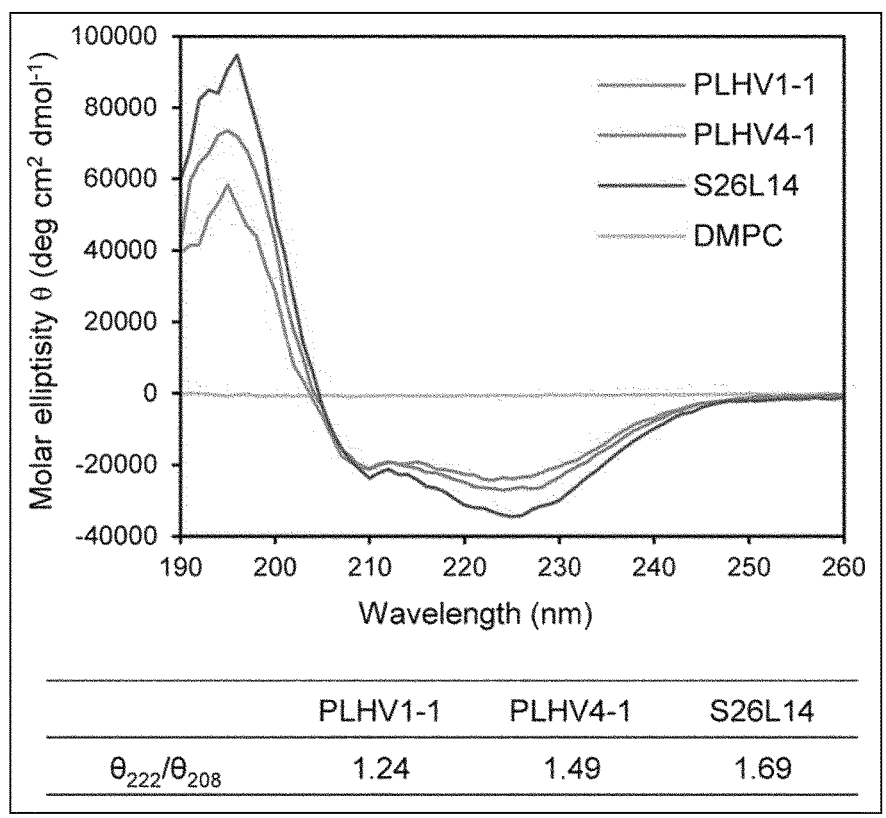
FIG. 7 shows the results of CD measurements in Example 2.
Figure 8:
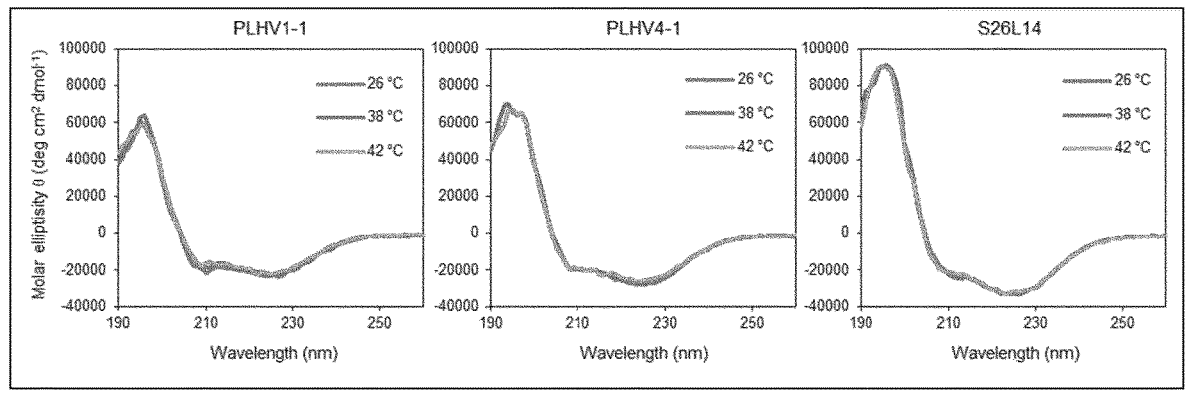
FIG. 8 shows the results of CD measurements in Example 2.

The results of CD measurements are shown in FIGS. 7 and 8.

Circular dichroism (CD) spectra of PLHV1-1, PLHV4-1, S26L14 nanotube, and DMPC liposome dispersions supported the presence of a peptide domain in the hybrid vesicles. The data revealed that both S26L14 peptide nanotubes and PLHVs displayed the characteristics of α-helical configurations, with double minima at 222 nm and 208 nm (FIG. 7). The $\theta_{222}/\theta_{208}$ ratios of PLHV1-1, PLHV4-1, and S26L14 nanotubes were 1.24, 1.49, and 1.69, respectively. The strict packing of S26L14 is evident because the ratio value >1 indicates a bundle formation of α-helices (Reference Literatures 6 and 7). The observed decrease of the $\theta_{222}/\theta_{208}$ ratio for the PLHVs is because DMPC inserted into the S26L14 membrane loosens the packing of the nanotube-forming S26L14. This results in PLHV1-1 and PLHV4-1 not forming nanotubes but spherical vesicles. Furthermore, CD spectra of PLHV1-1, PLHV4-1, and S26L14 assemblies at 26° C., 38° C., and 42° C. showed that temperature did not influence the secondary structure and bundle formation of the peptides (FIG. 8).

Example 3

Phase Separation and Phase Transition (Spectrofluorometer)

The fluorescent spectra of assembled dispersions were obtained using a JASCO FP-6500 spectrofluorometer (manufactured by JEOL) at 25° C. with a transmission cell.

(Forster Resonance Energy Transfer (FRET) Analysis)

To investigate the homo-/heterogeneity of PLHVs, fluorescence resonance energy transfer (FRET) analysis was performed using N-(7-nitro-2-1,3-benzoxadiazol-4-yl)-1,2-dipalmitoyl-sn-glycero-3-phosphoethanolamine (NBD-PE) and N-(lissamine rhodamine B sulfonyl)-1,2-dipalmitoyl-sn-glycero-3-phosphoethanolamine (Rhod-PE). NBD-PE and Rhod-PE act as the donor and acceptor for FRET measurements, respectively FRET experiments in vesicles were carried out using a fluorometer (Microplate Flash Reader, PerkinElmer, Waltham, Mass., USA). For the NBD-PE/Rhodamine (Rhod)-PE donor/acceptor pair, the excitation wavelength was set at 460 nm and emission spectra were collected from 480 to 650 nm. FRET was measured in liposomes containing known concentrations of donor- and acceptor-labeled vesicles.

Hybrid vesicles were labeled with 0.8 mol % of both NBD-PE and Rhod-PE. Briefly, for hybrid vesicles composed of polypeptides and DMPC, stock ethanol solutions of S26L14, DMPC, NBD-PE and Rhod-PE were mixed to give the desired ratio (S26L14:DMPC:NBD-PE:Rhod-PE=73: 73:0.58:0.58 or 0 nmol) and then added (injected) into physiological saline (1 mL) simultaneously. In this way, PLHV1-1 samples each of which contains S26L14 (73 nmol), DMPC (73 nmol), and NBD-PE (0.58 nmol) and each of which contains or does not contain Rhod-PE (0.58 nmol) were prepared. The mixture was then stirred and heated in the same manner as described in Example 1. Similarly, two kinds of DMPC liposome samples containing NBD-PE and Rhod-PE were prepared for FRET analysis as control samples with particular mixing ratios (DMPC:NBD-PE:Rhod-PE=73:0.58:0.58 or 0 nmol, and DMPC:NBD-PE: Rhod-PE=146:0.58:0.58 or 0 nmol). Hereinafter, 73 nmol/ mL DMPC liposome which contains NBD-PE (0.58 nmol) and which contains or does not contain Rhod-PE (0.58 nmol) may be referred to as "DMPC-73", and 146 nmol/mL DMPC liposome which contains NBD-PE (0.58 nmol) and which contains or does not contain Rhod-PE (0.58 nmol) may be referred to as "DMPC-146". In addition, respective donor-labeled (NBD-PE only) vesicles were also prepared to calculate the FRET efficiency E in the absence and presence of the acceptor according to the following equation (1).

$$E(\%) = (I_D - I_{DA})/(I_D) \times 100 \quad (1)$$

where $I_D$ and $I_{DA}$ are the donor intensities of samples containing only donor-labeled vesicles and samples with both donor- and acceptor-labeled vesicles, respectively.

(Laurdan Test)

The membrane fluidity of PLHVs, S26L14 nanotubes and DMPC liposomes was measured with N,N-dimethyl-6-dodecanoyl-2-naphthylamine (Laurdan). Laurdan is a fluorescent dye that is highly sensitive to the polarity of its surrounding environment. A general polarization value, $GP_{340}$, is calculated using the following equation (2):

$$GP_{340} = (I_{440} - I_{490})/(I_{440} + I_{490}) \quad (2)$$

where $I_{440}$ and $I_{490}$ are emission intensities at 440 nm and 490 nm of excited Laurdan at 340 nm. The temperature range of 10 to 42° C. was controlled by a circulating water bath.

(Differential Scanning Calorimetry (DSC))

DSC is used widely to detect the phase transition of liposomes and other molecules. Desired concentrations of 20 µL of self-assembled hybrid vesicles, DMPC liposomes, or peptide nanotubes were placed on aluminum pans that were sealed with lids. A reference sample pan with physiological saline only was also used. The temperature range for scanning samples was 10 to 60° C. with a heating rate of 1° C./min.

(Results and Consideration: Phase Separation)

Figure 9:
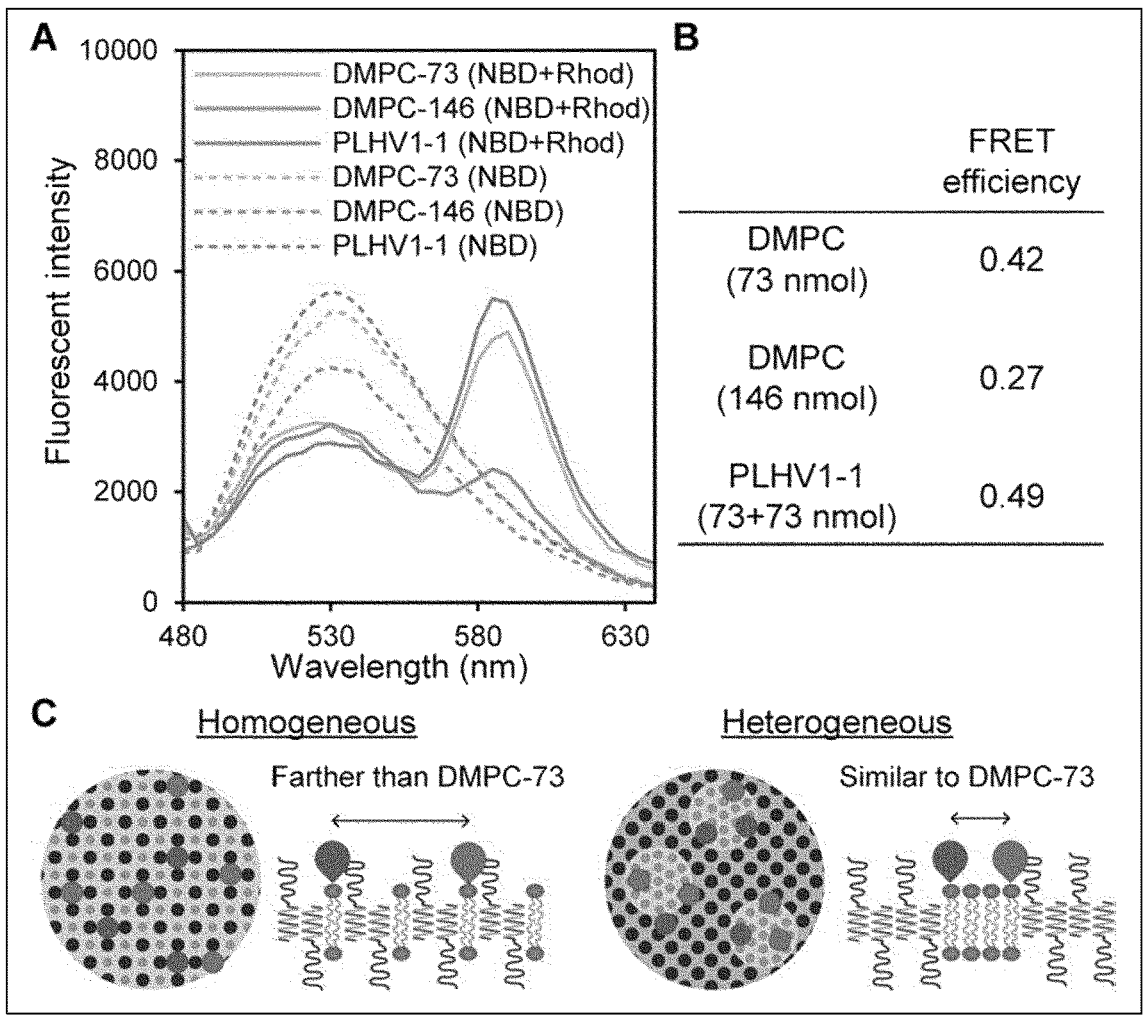
FIG. 9 shows the results of FRET analysis in Example 3.
Figure 10:
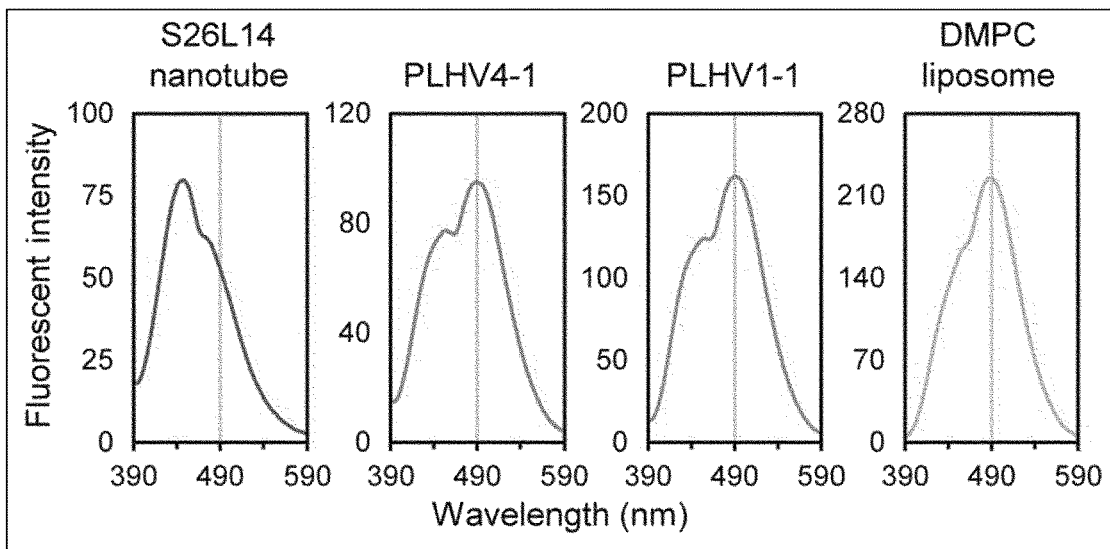
FIG. 10 shows the results of Laurdan test in Example 3.

The results of FRET analysis are shown in FIG. 9, and the results of Laurdan test are shown in FIG. 10.

Excitation of NBD-PE at 460 nm gave fluorescent spectra with a strong emission intensity of Rhod-PE in PLHV1-1 (A of FIG. 9), and the FRET efficiency was similar to that of the DMPC-73 dispersion (B of FIG. 9). Although the concentrations of FRET dye pairs in PLHV1-1 and DMPC-146 are the same, the FRET efficiency was close to that of the higher dye/lipid ratio system DMPC-73 (C of FIG. 9). This demonstrated that PLHV1-1 had a heterogeneous phase-separated membrane and both DMPC and S26L14 domains existed, as shown in C of FIG. 9.

Laurdan reagent (N,N-dimethyl-6-dodecanoyl-2-naphthyl-amine) can also be used as a molecular probe to monitor the heterogeneity of liposomes (Reference Literatures 8 to 10). Laurdan shows specific emission peaks at 440 nm and 490 nm that originate from lipid membranes in liquid ordered (Lo) and liquid disordered phases (Ld), respectively (Reference Literatures 9 and 10). FIG. 10 shows the fluorescence spectra of Laurdan in PLHV1-1, PLHV4-1, S26L14 nanotube, and DMPC liposomes dispersions at 42° C. A single peak at 490 nm was observed in the DMPC dispersion, whereas a single peak at 440 nm was observed in the S26L14 nanotube dispersion. These results indicated that DMPC liposomes and S26L14 nanotubes were in homogeneously disordered and ordered phases, respectively. In contrast, PLHV1-1 and PLHV4-1 exhibited emission peaks at both 440 nm and 490 nm, indicating the coexistence of disordered DMPC domains and ordered S26L14 domains in the hybrid vesicles.

(Results and Consideration: Phase Transition)

The generalized polarization, $GP_{340}$, value, which was calculated from emission intensities of Laurdan at 440 nm and 490 nm by using excitation light at 340 nm, has been shown to be a useful indicator of the degree of hydration of the membrane surface (equation (2)) (Reference Literatures 11 and 12). Investigating the $GP_{340}$ value as a function of temperature provided an approach to evaluate the phase transition temperature. The $GP_{340}$ value of S26L14 nanotubes from 10 to 42° C. was constant, indicating no phase-transition temperature ($T_m$) over this temperature range (A of FIG. 11). In contrast, the $GP_{340}$ value for DMPC showed a drastic change at temperatures equal to and below 25° C., which corresponds to the known $T_m$ of DMPC. The $GP_{340}$ value for PLHV1-1 and PLHV4-1 showed a decrease at temperatures equal to and below 35° C. To confirm the phase transition of the membrane, differential scanning calorimetry (DSC) measurements were also performed. The thermograms of PLHV1-1 and DMPC liposomes indicated that PLHV1-1 has a phase-transition temperature of 38° C., and DMPC liposomes have a value of a temperature equal to or below 23° C. (B of FIG. 11). Furthermore, the results from DSC analysis also showed that the S26L14 nanotube had no phase transition temperature from 14 to 46° C. (B of FIG. 11). As mentioned above, CD spectra of PLHV at various temperatures (FIG. 8) indicated that 42° C. did not affect the secondary structure of the peptide and bundle formation between peptides in PLHV. By taking these results into consideration, a phase transition of a hybrid vesicle corresponding to a lipid domain and S26L14 did not influence the spectra.

This phase transition of PLHV at 38° C. was attributed to the DMPC domain, because PLHV has phase-separated DMPC and S26L14 domains and the S26L14 domain had no $T_m$ over the foregoing temperature range. The large $T_m$ shift of 13° C. arises from the small DMPC domain, which is surrounded by the rigid helix bundle domain of S26L14. Reference Literatures 13 and 14 have reported that smaller lipid domain sizes show higher $T_m$ values using various-sized lipid nanodiscs. According to these studies, the $T_m$ shift of 10° C. was because of a loss of cooperativity in the lipids of domains, which was attributed to its small size and the interaction of boundary lipids with the environment of the surrounding domain. It is postulated that the additional 3° C. $T_m$ shift arises from the small fraction of peptide that has been inserted into the lipid domain or because of the rigidness of the peptide membrane surrounding the lipid domain.

Figure 11:
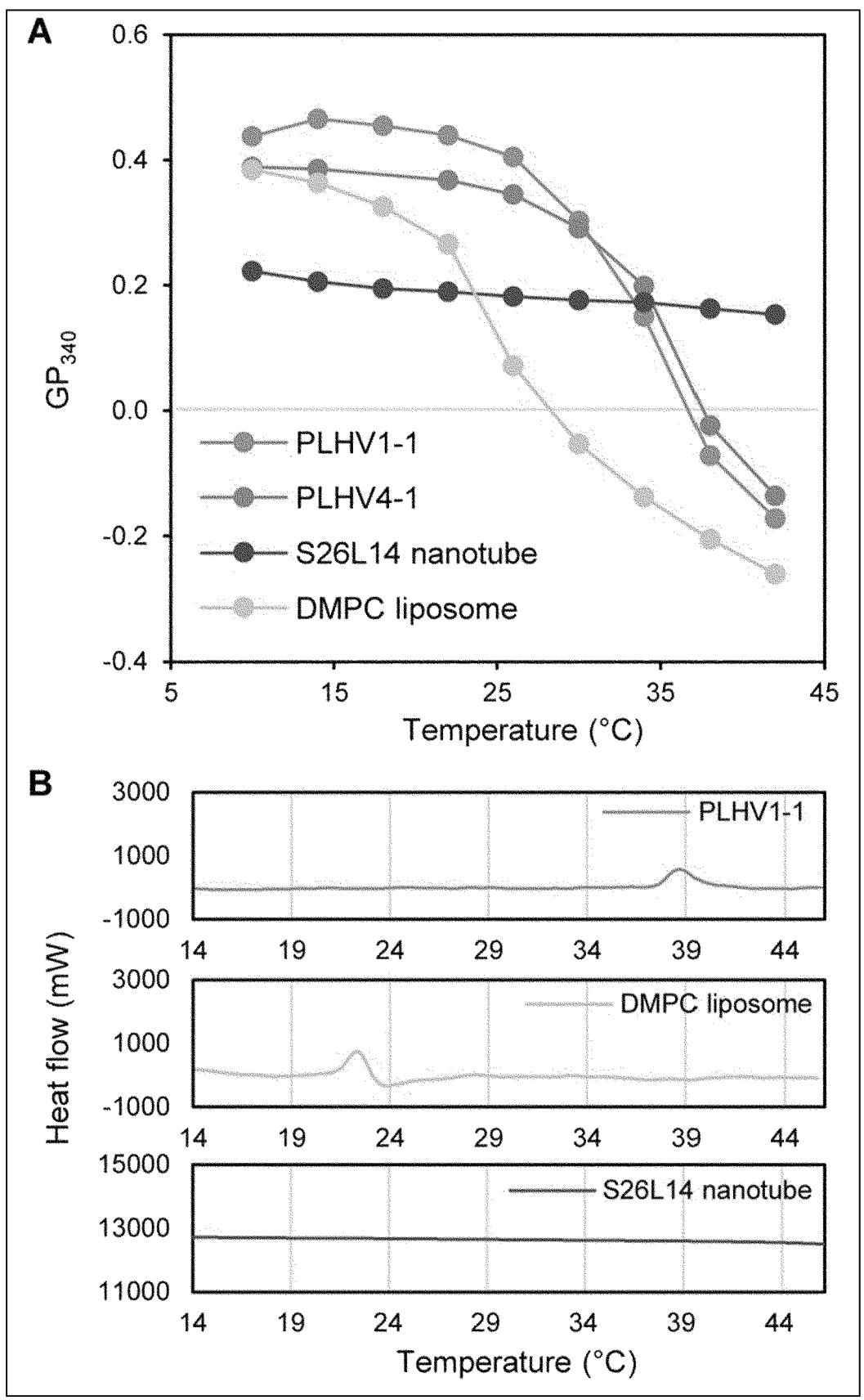
FIG. 11 shows the results of Laurdan test and DSC measurements in Example 3.

Interestingly, according to the Laurdan test, PLHV4-1 showed a slightly larger shift of the phase-transition temperature when compared to that of PLHV1-1 (A of FIG. 11). There are two possible models of PLHVs to consider when accounting for this slight phase-transition shift: vesicles with smaller sized lipid domains or vesicles with a smaller number of lipid domains in the PLHVs. Because the number of domains cannot influence the phase transition, it was concluded that the DMPC domains in PLHV4-1 are smaller than those present in PLHV1-1.

Example 4

Release Study (Synthesis of FITC-PEG2K and FITC-PEG5K)

A method of synthesis of FITC-PEG2K and FITC-PEG5K, and the NMR and MS spectra of the obtained FITC-PEG2K and FITC-PEG5K, are shown below.

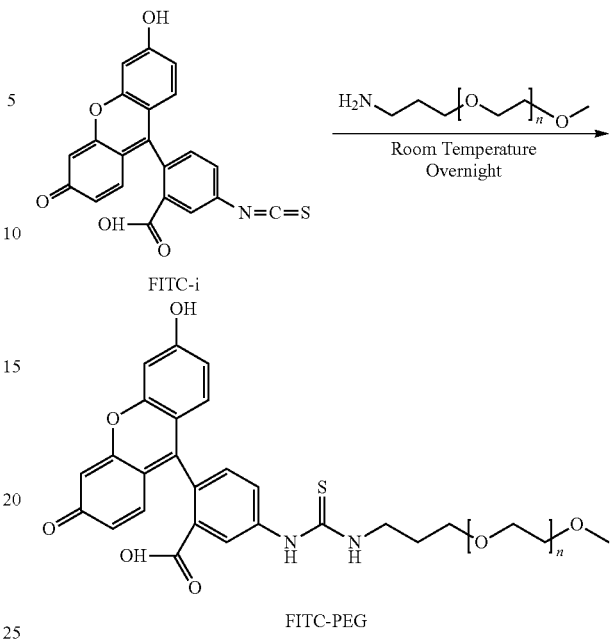

NMR and MS Spectra of FITC-PEG2K $^1$HNMR (400 MHz, CDCl$_3$) δ (ppm) 7.99-6.54 (m, FITC), 3.88 (m, 2H, PEG-CH$_2$), 3.66 (PEG-CH$_2$CH$_2$), 3.40 (s, 3H, PEG-OCH$_3$). MALDI-TOF MS calculated for $C_{113}H_{198}N_2O_{51}SNa^+[M+Na]^+$m/z 2454.27; found:2454.14.

NMR and MS Spectra of FITC-PEG5K $^1$HNMR (400 MHz, CDCl$_3$) δ (ppm) 7.98-6.56 (m, FITC), 3.88 (m, 2H, PEG-CH$_2$), 3.65 (PEG-CH$_2$CH$_2$), 3.38 (s, 3H, PEG-OCH$_3$). MALDI-TOF MS calculated for $C_{249}H_{471}N_2O_{119}S^+[M+H]^+$m/z 5426.05; found: 5427.59.

(FITC-PEG Loading and Release Study)

Three millimolar, which is a concentration that shows self-quenching property, of FITC-PEG was used to investigate the loading and release characteristics of PLHVs. Desired molar ratios of hybrid vesicles and DMPC liposome stock solutions were added (injected) into physiological saline containing FITC-PEG and stirred for 2 hours, and then heated at 90° C. for 1 hour. The samples were then passed through a Millipore centrifuge filter unit (30 kDa molecular weight cutoff) using a centrifugation speed of 2000 rpm at 4° C. to remove free FITC-PEG. The loading efficiency of FITC-PEG was calculated as shown in the following equation (3):

$$(F_{af}/F_{bf}) \times 100 \qquad (3)$$

where $F_{af}$ is fluorescence intensity after the centrifuge filter pass and $F_{bf}$ is fluorescence intensity before the centrifuge filter pass. The fluorescence dequenching assay was used to determine the FITC-PEG release from hybrid vesicles and DMPC liposomes. In brief, 100 µL of FITC-PEG-loaded hybrid vesicles or DMPC liposomes were added (injected) into 20 mL of physiological saline and mixed homogeneously. At 0.5, 1, 2 and 4 hour intervals, 1 mL of the samples were taken and cooled on ice to stop further drug release. The release rate of FITC-PEG was calculated using the following equation (4):

$$\text{Release rate (\%)} = (F-F_0)/(F_{100}-F_0) \times 100 \qquad (4)$$

where F is the fluorescence intensity of the sample at a specific point, $F_0$ is the background fluorescence of the sample and $F_{100}$ is the maximum fluorescence release from the lysed carrier by lysis buffer, which was the average of three samples. Lysis buffer (Code #CK12, Lot. KU749, Dojindo Molecular Technologies, INC., Japan) (5 μL) was added to FITC-PEG loaded hybrid vesicle dispersions (1 mL), and dispersions were heated at 60° C. for 10 minutes to obtain the $F_{100}$ value. A JASCO FP-6500 fluorescence spectrometer (manufactured by JEOL) was used with excitation and emission wavelengths of 490 nm and 520 nm, respectively. The temperatures used for this release study were 4° C., 37° C. and 42° C. The molecular weight of PEG was 2 and 5 kDa.

(Results and Consideration)

Figure 12:
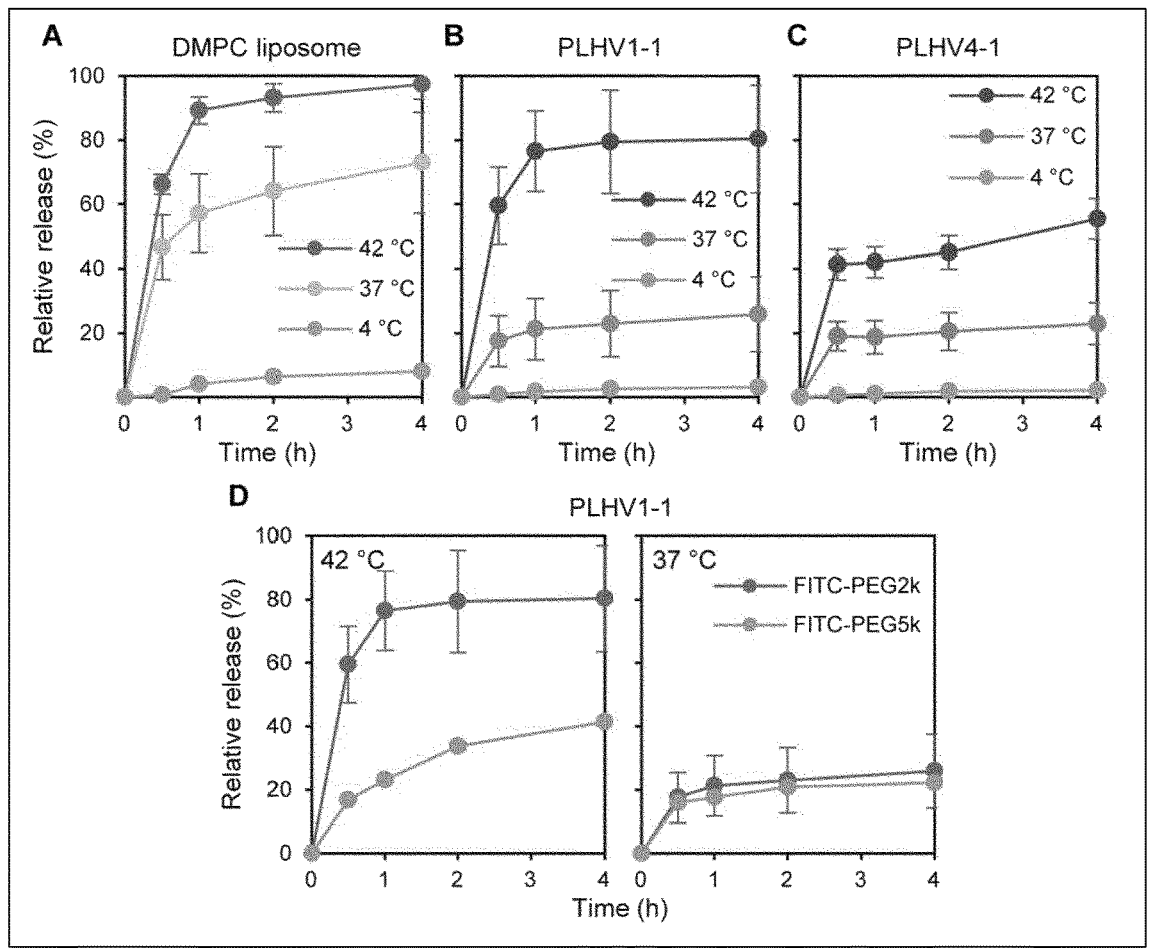
FIG. 12 shows the results of release study in Example 4.
Figure 13:
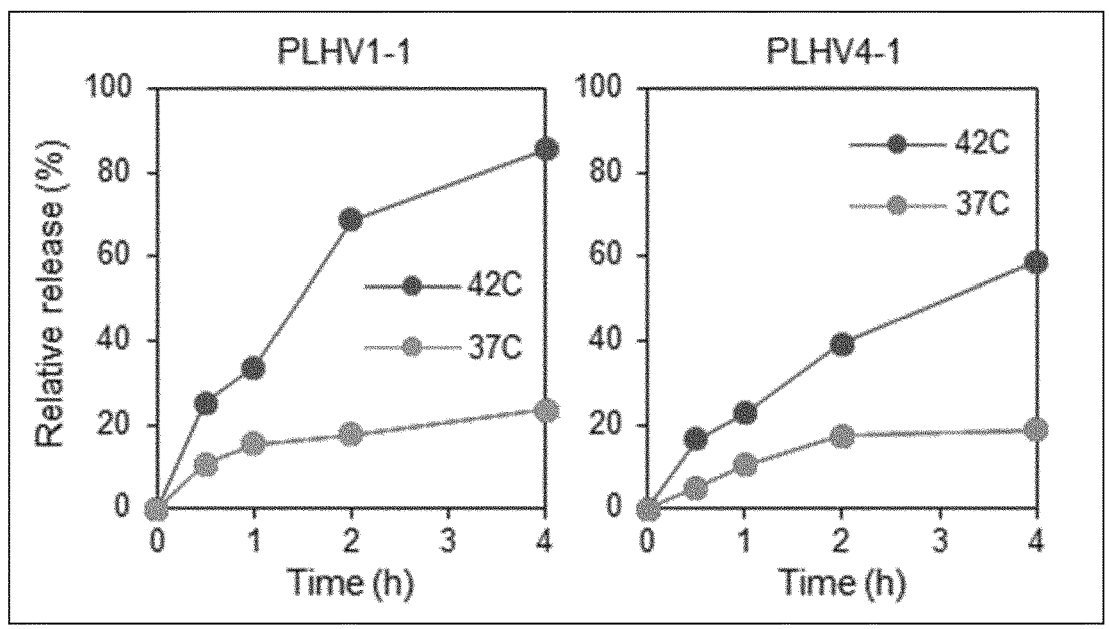
FIG. 13 shows the results of release study in Example 4.
Figure 14:
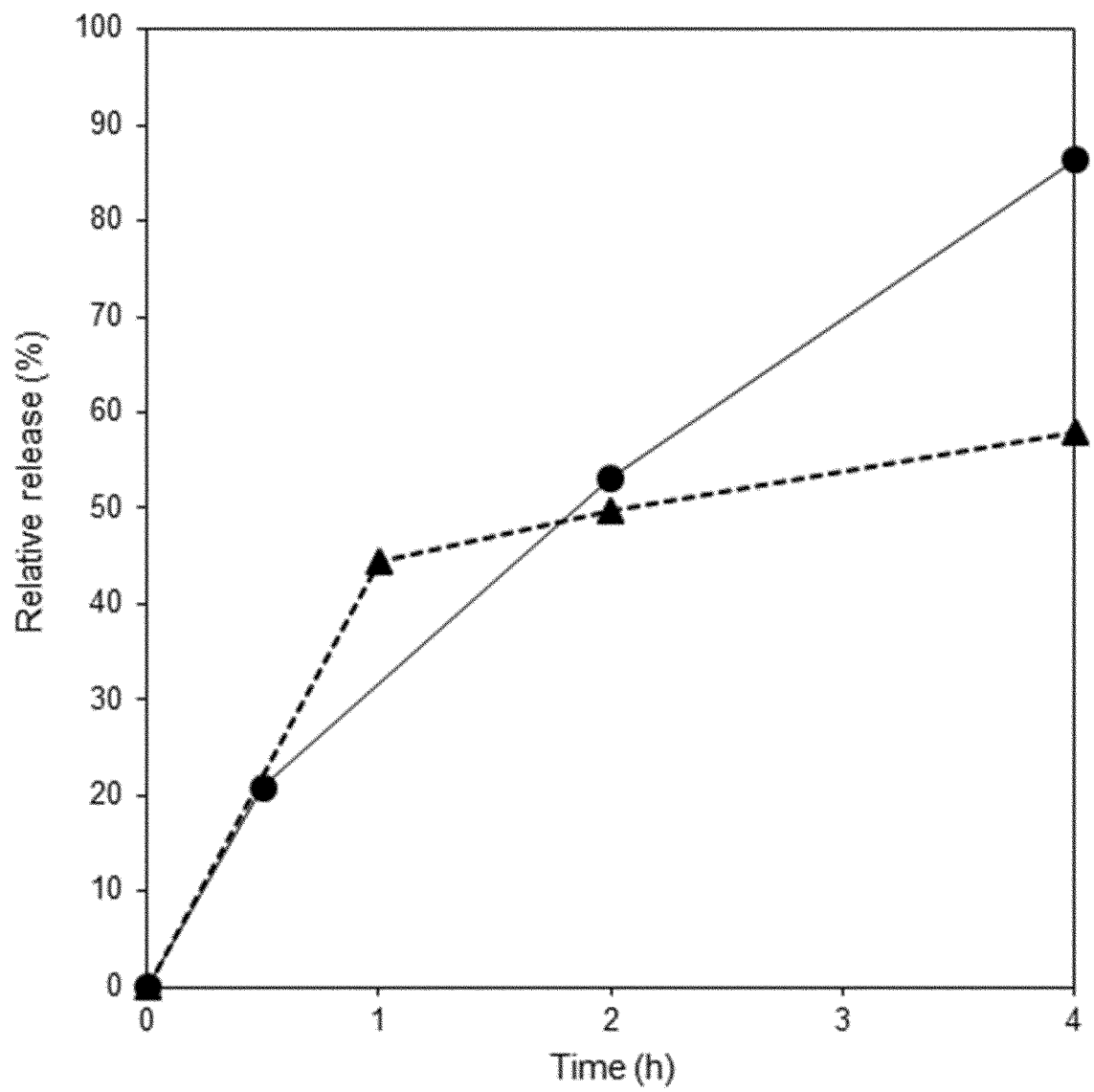
FIG. 14 shows the results of release study in Example 4.

Fluorescein isothiocyanate-labeled polyethylene glycol (Mw: 2000) (FITC-PEG2K) was encapsulated into PLHVs with a sufficiently high FITC-PEG2K concentration to quench fluorescence of FITC. Releasing efficiencies of FITC-PEG2K with DMPC liposomes, PLHV1-1, and PLHV4-1 were 3.9%, 7.1%, and 5.8%, respectively. FITC-PEG2K release experiments were carried out at 4° C., 37° C., and 42° C. As shown in FIG. 12, FITC-PEG2K was released as a function of time under a constant temperature. Encapsulation of FITC-PEG2K was maintained for 4 hours at 4° C. for all the foregoing assemblies (A to C of FIG. 12). For DMPC liposomes, more than 70% of FITC-PEG2K was released rapidly at 37° C. and 42° C. This is because the DMPC liposomes are in a disordered phase at 37° C. and 42° C. (FIG. 11). In contrast, PLHV1-1 released FITC-PEG2K only at 42° C. (B of FIG. 12), and FITC-PEG2K remained encapsulated at 37° C. because 37° C. is lower than the $T_m$. Thus, the DMPC domain acted as a temperature-responsive gate. For PLHV4-1, in a similar manner, FITC-PEG2K was not released at 37° C. However, at 42° C., slow release was observed (C of FIG. 6). Presumably, the smaller DMPC domain size reduced the release rate of FITC-PEG2K from PLHV4-1. Furthermore, another small hydrophilic dye, sulforhodamine B (SRB), also remained trapped inside the nanoparticles at 37° C. and was released at 42° C. from PLHV1-1 and PLHV4-1 (FIG. 13). After being heated at 42° C. for 4 hours, greater release of SRB was observed than that of FITC-PEG2K. These results also support that the lipid domain size can potentially define the size and release rate of trapped material. Therefore, this result indicates that a hybrid vesicle can entrap and release drugs. The release kinetics of the fluorescein isothiocyanate-labeled polyethylene glycol (Mw: 5000) (FITC-PEG5K), which has a larger molecular weight, was evaluated. The release of FITC-PEG5K from PLHV1-1 was suppressed at 42° C. (D of FIG. 12). In contrast, DMPC liposomes leaked FITCPEG5K equally to FITC-PEG2K at both 37° C. (broken line) and 42° C. (solid line) (FIG. 14).

LIST OF REFERENCE LITERATURES (1) M. Ueda, A. Makino, T. Imai, J. Sugiyama and S. Kimura, Polym. J. 2013, 45, 509-515

(2) T. Kanzaki, Y. Horikawa, A. Makino, J. Sugiyama and S. Kimura, Macromol. Biosci. 2008, 8(11), 1026-1033

(3) Kaindl, T.; Adlkofer, K.; Morita, T.; Umemura, J.; Konovalov, O.; Kimura, S.; Tanaka, M. Modulation of Band Bending of Gallium Arsenide with Oriented Helical Peptide Monolayers. J. Phys. Chem. C 2010, 114 (51), 22677-22683

(4) Nakano, M.; Fukuda, M.; Kudo, T.; Miyazaki, M.; Wada, Y.; Matsuzaki, N.; Endo, H.; Handa, T. Static and Dynamic Properties of Phospholipid Bilayer Nanodiscs. J. Am. Chem. Soc. 2009, 131 (23), 8308-8312

(5) Lewis, B. A.; Engelman, D. M. Lipid Bilayer Thickness Varies Linearly with Acyl Chain-Length in Fluid Phosphatidylcholine Vesicles. J. Mol. Biol. 1983, 166 (2), 211-217

(6) Kornilova, A. Y.; Wishart, J. F.; Xiao, W. Z.; Lasey, R. C.; Fedorova, A.; Shin, Y. K.; Ogawa, M. Y. Design and characterization of a synthetic electron-transfer protein. J. Am. Chem. Soc. 2000, 122 (33), 7999-8006

(7) Cohen, C.; Parry, D. A. D. Alpha-Helical Coiled Coils and Bundles—How to Design an Alpha-Helical Protein. Proteins: Struct., Funct., Genet. 1990, 7 (1), 1-15

(8) Parasassi, T.; Krasnowska, E. K.; Bagatolli, L.; Gratton, E. LAURDAN and PRODAN as polarity-sensitive fluorescent membrane probes. J. Fluoresc. 1998, 8 (4), 365-373

(9) Parasassi, T.; Gratton, E. Membrane lipid domains and dynamics as detected by Laurdan fluorescence. J. Fluoresc. 1995, 5 (1), 59-69

(10) Parasassi, T.; De Stasio, G.; Ravagnan, G.; Rusch, R. M.; Gratton, E. Quantitation of Lipid Phases in Phospholipid-Vesicles by the Generalized Polarization of Laurdan Fluorescence. Biophys. J. 1991, 60 (1), 179-189

(11) Bakht, O.; Pathak, P.; London, E. Effect of the structure of lipids favoring disordered domain formation on the stability of cholesterol-containing ordered domains (lipid rafts): Identification of multiple raft-stabilization mechanisms. Biophys. J. 2007, 93 (12), 4307-4318

(12) Viard, M.; Gallay, J.; Vincent, M.; Meyer, O.; Robert, B.; Paternostre, M. Laurdan solvatochromism: Solvent dielectric relaxation and intramolecular excited-state reaction. Biophys. J. 1997, 73 (4), 2221-2234

(13) Denisov, I. G.; McLean, M. A.; Shaw, A. W.; Grinkova, Y. V.; Sligar, S. G. Thermotropic phase transition in soluble nanoscale lipid bilayers. J. Phys. Chem. B 2005, 109 (32), 15580-15588

(14) Shaw, A. W.; McLean, M. A.; Sligar, S. G. Phospholipid phase transitions in homogeneous nanometer scale bilayer discs. FEBS Lett. 2004, 556 (1-3), 260-264

The contents of Reference Literatures (1) to (14) and the documents cited in the present specification are incorporated herein by reference.

INDUSTRIAL APPLICABILITY

A nanostructure of the present invention can be used widely in the fields of pharmaceuticals, food, cosmetics, and the like as, for example, a carrier to transport an agent into cells.

The invention claimed is:

1. A nanostructure which is a hollow body constituted by a wall, the wall consisting of a first wall and a second wall, the first wall being formed from an assembly of a plurality of first amphiphilic molecules containing a hydrophilic block and a hydrophobic block, the second wall consisting of one or more regions which are formed from an assembly of a plurality of second amphiphilic molecules, and distributed by phase separation in the first region forming a gate between an outer surface and an inner surface of the hollow body separately wherein, the first amphiphilic molecule is an amphiphilic peptide chain represented by the following Formula (I)

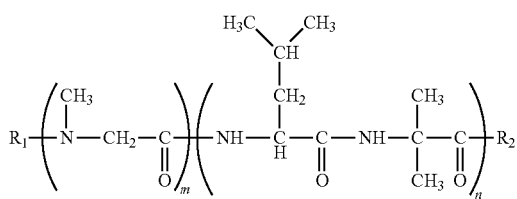 (1)

wherein m is 5 to 80, n is 4 to 15, $R_1$ is ketole group or an acetyl group, and $R_2$ is a $C_1$-$C_4$ alkoxy group or a benzyl ester group; and the second amphiphilic molecule is a phospholipid molecule selected from the group consisting of 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-dilauroyl-sn-glycero-3-phosphocholine (DLPC), and 1,2-dioleoyl-sn-glycero-3-phosphocholine (DOPC), wherein the ratio of surface area occupied by the first amphiphilic molecules to surface area occupied by the second amphiphilic molecules is 69:31 to 90:10.

2. The nanostructure as set forth in claim 1, wherein the hydrophobic peptide block has a helix structure.

3. The nanostructure as set forth in claim 1, wherein the first amphiphilic molecules is S26L14, and the second amphiphilic molecules is DMPC.

4. The nanostructure as set forth in claim 1, wherein the nanostructure has an agent retained therein.

5. A pharmaceutical composition comprising a nanostructure recited in claim 4.

6. A method of producing a nanostructure recited in claim 1, the method comprising
a step of preparing a hollow body by heating an aqueous medium that contains the first amphiphilic molecules and the second amphiphilic molecules.

* * * * *